US011331316B2

(12) United States Patent
Li

(10) Patent No.: US 11,331,316 B2
(45) Date of Patent: May 17, 2022

(54) AMORPHOUS SOLID DISPERSIONS

(71) Applicant: INTRA-CELLULAR THERAPIES, INC., New York, NY (US)

(72) Inventor: Peng Li, New Milford, NJ (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 65 days.

(21) Appl. No.: 16/341,806

(22) PCT Filed: Oct. 3, 2017

(86) PCT No.: PCT/US2017/054962
§ 371 (c)(1),
(2) Date: Apr. 12, 2019

(87) PCT Pub. No.: WO2018/071233
PCT Pub. Date: Apr. 19, 2018

(65) Prior Publication Data
US 2019/0388418 A1 Dec. 26, 2019

Related U.S. Application Data

(60) Provisional application No. 62/407,285, filed on Oct. 12, 2016.

(51) Int. Cl.
| | | |
|---|---|---|
| *A61K 31/4985* | (2006.01) |
| *A61K 9/20* | (2006.01) |
| *A61K 9/16* | (2006.01) |
| *A61K 9/00* | (2006.01) |
| *A61K 47/38* | (2006.01) |
| *A61P 25/28* | (2006.01) |
| *A61P 25/22* | (2006.01) |
| *A61P 3/04* | (2006.01) |
| *A61P 25/18* | (2006.01) |
| *A61P 25/24* | (2006.01) |
| *A61P 25/06* | (2006.01) |
| *A61K 9/48* | (2006.01) |
| *C07D 471/16* | (2006.01) |
| *A61K 9/10* | (2006.01) |

(52) U.S. Cl.
CPC ........ *A61K 31/4985* (2013.01); *A61K 9/0019* (2013.01); *A61K 9/0024* (2013.01); *A61K 9/0053* (2013.01); *A61K 9/1617* (2013.01); *A61K 9/1635* (2013.01); *A61K 9/1641* (2013.01); *A61K 9/1652* (2013.01); *A61K 9/2013* (2013.01); *A61K 9/2027* (2013.01); *A61K 9/2031* (2013.01); *A61K 9/2054* (2013.01); *A61K 9/4858* (2013.01); *A61K 9/4866* (2013.01); *A61K 47/38* (2013.01); *A61P 3/04* (2018.01); *A61P 25/06* (2018.01); *A61P 25/18* (2018.01); *A61P 25/22* (2018.01); *A61P 25/24* (2018.01); *A61P 25/28* (2018.01); *A61K 9/10* (2013.01); *C07D 471/16* (2013.01)

(58) Field of Classification Search
CPC .......... A61K 9/06; A61K 9/10; A61K 9/0024; A61K 9/1652; A61K 9/2054; A61K 47/00; A61K 31/4985; A61K 9/0053; A61K 9/4858; A61K 9/16; A61K 9/4825; A61K 9/485; A61K 9/4891; A61K 9/2013; A61K 47/38; A61K 9/0019; A61K 9/1617; A61K 9/1635; A61K 9/1641; A61K 9/2027; A61K 9/2031; A61K 9/4866; A61K 45/06; A61K 9/20; A61K 9/2009; A61K 9/284; A61K 9/48; C07D 471/16
See application file for complete search history.

(56) References Cited

U.S. PATENT DOCUMENTS

| | | | |
|---|---|---|---|
| 2,490,813 | A | 12/1949 | Hughes et al. |
| 3,299,078 | A | 1/1967 | Pachter |
| 3,813,392 | A | 5/1974 | Sellstedt et al. |
| 3,914,421 | A | 10/1975 | Rajagopalan |
| 4,001,263 | A | 1/1977 | Plattner et al. |
| 4,115,577 | A | 9/1978 | Rajagopalan |
| 4,183,936 | A | 1/1980 | Rajagopalan |
| 4,219,550 | A | 8/1980 | Rajagopalan |
| 4,238,607 | A | 12/1980 | Rajagopalan |
| 4,389,330 | A | 6/1983 | Tice et al. |
| 4,522,944 | A | 6/1985 | Doria et al. |
| 4,530,840 | A | 7/1985 | Tice et al. |
| 4,971,971 | A | 11/1990 | Tokunaga et al. |
| 4,985,432 | A | 1/1991 | Tokunaga et al. |
| 5,114,976 | A | 5/1992 | Norden |

(Continued)

FOREIGN PATENT DOCUMENTS

| | | |
|---|---|---|
| CN | 102105059 A | 6/2011 |
| CN | 103209704 A | 7/2013 |

(Continued)

OTHER PUBLICATIONS

Mooter, title: The use of amorphous solid dispersions: A formulation strategy to overcome poor solubility and dissolution rate; Drug Discovery Today: Technologies; vol. 9, Issue 2, Summer 2012, pp. e79-e85 (Year: 2012).*

(Continued)

*Primary Examiner* — Audrea B Coniglio
(74) *Attorney, Agent, or Firm* — Hoxie & Associates LLC

(57) ABSTRACT

The disclosure provides new, stable, pharmaceutically acceptable amorphous solid dispersions of 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one, together with methods of making and using them, and pharmaceutical compositions comprising them.

20 Claims, 6 Drawing Sheets

(56) References Cited

U.S. PATENT DOCUMENTS

| | | |
|---|---|---|
| 5,151,419 A | 9/1992 | Perenyi et al. |
| 5,538,739 A | 7/1996 | Bodmer et al. |
| 5,576,460 A | 11/1996 | Buchwald et al. |
| 5,648,539 A | 7/1997 | Goodbrand |
| 5,648,542 A | 7/1997 | Goodbrand et al. |
| 5,654,482 A | 8/1997 | Goodbrand |
| 5,705,697 A | 1/1998 | Goodbrand et al. |
| 5,723,669 A | 3/1998 | Goodbrand et al. |
| 5,723,671 A | 3/1998 | Goodbrand et al. |
| 5,847,166 A | 12/1998 | Buchwald et al. |
| 5,902,901 A | 5/1999 | Goodbrand et al. |
| 6,043,370 A | 3/2000 | Kubo et al. |
| 6,166,226 A | 12/2000 | Buchwald et al. |
| 6,235,936 B1 | 5/2001 | Buchwald et al. |
| 6,307,087 B1 | 10/2001 | Buchwald et al. |
| 6,323,366 B1 | 11/2001 | Wolfe et al. |
| 6,395,916 B1 | 5/2002 | Buchwald et al. |
| 6,407,092 B1 | 6/2002 | Hester et al. |
| 6,465,693 B2 | 10/2002 | Buchwald et al. |
| 6,541,639 B2 | 4/2003 | Zhou et al. |
| 6,548,493 B1 | 4/2003 | Robichaud et al. |
| 6,552,017 B1 | 4/2003 | Robichaud et al. |
| 6,699,852 B2 | 3/2004 | Robichaud et al. |
| 6,713,471 B1 | 3/2004 | Robichaud et al. |
| 6,759,554 B2 | 7/2004 | Buchwald et al. |
| 6,762,329 B2 | 7/2004 | Marcoux et al. |
| 6,828,314 B2 | 12/2004 | Frank et al. |
| 6,849,619 B2 | 2/2005 | Robichaud et al. |
| 6,849,640 B2 | 2/2005 | Ennis et al. |
| 6,867,298 B2 | 3/2005 | Buchwald et al. |
| 6,888,032 B2 | 5/2005 | Buchwald et al. |
| 6,946,560 B2 | 9/2005 | Buchwald et al. |
| 7,026,498 B2 | 4/2006 | Buchwald et al. |
| 7,071,186 B2 | 7/2006 | Robichaud et al. |
| 7,081,455 B2 | 7/2006 | Robichaud et al. |
| 7,109,339 B2 | 9/2006 | Lee et al. |
| 7,115,784 B2 | 10/2006 | Buchwald et al. |
| 7,183,282 B2 | 2/2007 | Robichaud et al. |
| 7,223,879 B2 | 5/2007 | Buchwald et al. |
| RE39,679 E | 6/2007 | Robichaud et al. |
| RE39,680 E | 6/2007 | Robichaud et al. |
| 7,238,690 B2 | 7/2007 | Robichaud et al. |
| 7,247,731 B2 | 7/2007 | Buchwald et al. |
| 7,323,608 B2 | 1/2008 | Buchwald et al. |
| 7,375,226 B2 | 5/2008 | Jolidon et al. |
| 7,462,641 B2 | 12/2008 | Igo et al. |
| 7,580,623 B2 | 8/2009 | Nuno et al. |
| 7,592,454 B2 | 9/2009 | Lee et al. |
| 7,598,273 B2 | 10/2009 | Gant et al. |
| 7,614,727 B2 | 11/2009 | Hori |
| 7,645,752 B2 | 1/2010 | McDevitt et al. |
| 7,750,168 B2 | 7/2010 | Poyten et al. |
| 7,998,971 B2 | 8/2011 | Barlow et al. |
| 8,309,722 B2 | 11/2012 | Tornesch et al. |
| 8,309,772 B2 | 11/2012 | Weiner et al. |
| 8,461,148 B2 | 6/2013 | Hollander |
| 8,598,119 B2 | 12/2013 | Mates et al. |
| 8,648,077 B2 | 2/2014 | Tornesch et al. |
| 8,779,139 B2 | 7/2014 | Tornesch et al. |
| 8,791,138 B2 | 7/2014 | Seeman et al. |
| 8,993,572 B2 | 3/2015 | Mates et al. |
| 9,168,258 B2 | 10/2015 | Mates et al. |
| 9,199,995 B2 | 12/2015 | Tornesch et al. |
| 9,315,504 B2 | 4/2016 | Tornesch et al. |
| 9,371,324 B2 | 6/2016 | Mates et al. |
| 9,393,192 B2 | 7/2016 | Yam et al. |
| 9,427,412 B2 | 8/2016 | Bryson et al. |
| 9,428,506 B2 | 8/2016 | Mates et al. |
| 9,567,327 B2 | 2/2017 | Xiong et al. |
| 9,586,960 B2 | 3/2017 | Tornesch et al. |
| 9,616,061 B2 | 4/2017 | Mates et al. |
| 9,708,322 B2 | 7/2017 | Li et al. |
| 9,745,300 B2 | 8/2017 | Mates et al. |
| 9,751,883 B2 | 9/2017 | Tornesch et al. |
| 9,956,227 B2 | 5/2018 | Vanover et al. |
| 10,072,010 B2 | 9/2018 | Li et al. |
| 10,077,267 B2 | 9/2018 | Mates et al. |
| 10,117,867 B2 | 11/2018 | Mates et al. |
| 10,350,196 B2 | 7/2019 | Foster et al. |
| 2001/0008942 A1 | 7/2001 | Buchwald et al. |
| 2003/0130206 A1 | 7/2003 | Koziak et al. |
| 2003/0225058 A1 | 12/2003 | Frank et al. |
| 2004/0013734 A1* | 1/2004 | Babcock .............. A61K 9/1635 424/488 |
| 2004/0034015 A1 | 2/2004 | Robichaud et al. |
| 2004/0092534 A1 | 5/2004 | Yam et al. |
| 2004/0127482 A1 | 7/2004 | Robichaud et al. |
| 2004/0142970 A1 | 7/2004 | Chung et al. |
| 2004/0186136 A1 | 9/2004 | Alken et al. |
| 2004/0220178 A1 | 11/2004 | Robichaud et al. |
| 2005/0166771 A1 | 8/2005 | Gygi et al. |
| 2005/0222209 A1 | 10/2005 | Zeldis et al. |
| 2005/0222238 A1 | 10/2005 | Alken |
| 2006/0178362 A1 | 8/2006 | Robichaud et al. |
| 2006/0205787 A1 | 9/2006 | Muller et al. |
| 2007/0082929 A1 | 4/2007 | Gant et al. |
| 2007/0203120 A1 | 8/2007 | McDevitt et al. |
| 2008/0069885 A1 | 3/2008 | Mesens et al. |
| 2008/0132552 A1 | 6/2008 | Kleinman et al. |
| 2008/0280941 A1 | 11/2008 | Lourtie |
| 2008/0303137 A1 | 12/2008 | Ward et al. |
| 2009/0076159 A1 | 3/2009 | Czarnik |
| 2009/0209608 A1 | 8/2009 | Czarnik |
| 2010/0159033 A1 | 6/2010 | Gant et al. |
| 2011/0020369 A1 | 1/2011 | De Waal Malefyt et al. |
| 2014/0004237 A1 | 1/2014 | Sander et al. |
| 2014/0080816 A1 | 3/2014 | Koolman et al. |
| 2014/0210117 A1* | 7/2014 | Friesen .............. A61K 9/146 264/5 |
| 2015/0004237 A1 | 1/2015 | Edgar et al. |
| 2015/0031804 A1 | 1/2015 | Shiramizu et al. |
| 2015/0071964 A1 | 3/2015 | Tang |
| 2015/0072964 A1* | 3/2015 | Mates .............. A61K 31/4985 514/171 |
| 2015/0080404 A1 | 3/2015 | Mates et al. |
| 2015/0166540 A1 | 6/2015 | Mates et al. |
| 2016/0031885 A1 | 2/2016 | Li et al. |
| 2016/0235720 A1 | 8/2016 | Foster et al. |
| 2016/0310502 A1 | 10/2016 | Vanover et al. |
| 2016/0354315 A1 | 12/2016 | Li |
| 2017/0114037 A1 | 4/2017 | Davis et al. |
| 2017/0319580 A1 | 11/2017 | Yao et al. |
| 2018/0200256 A1 | 7/2018 | Vanover et al. |
| 2019/0071445 A1 | 3/2019 | Li et al. |
| 2019/0183888 A1 | 6/2019 | Mates et al. |
| 2019/0211015 A1 | 7/2019 | Mittelman et al. |
| 2019/0231780 A1 | 8/2019 | Yao et al. |
| 2019/0388418 A1 | 12/2019 | Li |
| 2020/0148683 A1 | 5/2020 | Peddy et al. |

FOREIGN PATENT DOCUMENTS

| | | |
|---|---|---|
| EP | 0 058 481 | 8/1982 |
| EP | 0 856 508 | 8/1998 |
| EP | 0 976 732 | 2/2000 |
| EP | 1 245 553 | 10/2002 |
| EP | 1 254 884 | 11/2002 |
| EP | 1 539 115 | 6/2005 |
| EP | 1 564 671 | 8/2005 |
| GB | 1476087 | 6/1977 |
| GB | 2145422 | 3/1985 |
| IN | 201741021763 | 12/2018 |
| WO | WO 1994/024125 | 10/1994 |
| WO | WO 1995/013814 | 5/1995 |
| WO | WO 1995/026325 | 10/1995 |
| WO | WO 1998/015515 | 4/1998 |
| WO | WO 1998/043956 | 10/1998 |
| WO | WO 1999/043643 | 9/1999 |
| WO | WO 2000/002887 | 1/2000 |
| WO | WO 2000/035419 | 6/2000 |
| WO | WO 2000/048610 | 8/2000 |
| WO | WO 2000/064899 | 11/2000 |
| WO | WO 2000/077001 | 12/2000 |
| WO | WO 2000/077002 | 12/2000 |

(56) References Cited

FOREIGN PATENT DOCUMENTS

| | | |
|---|---|---|
| WO | WO 2000/077010 | 12/2000 |
| WO | WO 2002/059129 | 8/2002 |
| WO | WO 2002/085838 | 10/2002 |
| WO | WO 2003/014118 | 2/2003 |
| WO | WO 2004/010981 | 2/2004 |
| WO | WO 2004/013094 | 2/2004 |
| WO | WO 2004/039788 | 5/2004 |
| WO | WO 2004/056324 | 7/2004 |
| WO | WO 2004/06473 8 | 8/2004 |
| WO | WO 2005/030214 | 4/2005 |
| WO | WO 2006/034187 | 3/2006 |
| WO | WO 2006/081251 | 8/2006 |
| WO | WO 2006/081332 | 8/2006 |
| WO | WO 2007/025103 | 3/2007 |
| WO | WO 2007/084841 | 7/2007 |
| WO | WO 2008/112280 | 9/2008 |
| WO | WO 2009/017836 | 2/2009 |
| WO | WO 2009/114181 | 9/2009 |
| WO | WO 2009/145900 | 12/2009 |
| WO | WO 2011/133224 | 10/2011 |
| WO | WO 2013/155504 | 10/2013 |
| WO | WO 2013/155505 | 10/2013 |
| WO | WO 2013/155506 | 10/2013 |
| WO | WO 2014/145192 | 9/2014 |
| WO | WO 2015/085004 | 6/2015 |
| WO | WO 2015/154025 | 10/2015 |
| WO | WO 2015/154030 | 10/2015 |
| WO | WO 2015/191554 | 12/2015 |
| WO | WO 2017/132408 | 8/2017 |
| WO | WO 2017/165755 | 9/2017 |
| WO | WO 2017/165843 | 9/2017 |
| WO | WO 2018/106916 | 6/2018 |
| WO | WO 2019/102240 | 5/2019 |
| WO | WO 2019/178484 | 9/2019 |

OTHER PUBLICATIONS

Cellulose acete, product information, downloaded from PubChem on Nov. 3, 2020. (Year: 2020).*
Cellulose acete phthalate, product information, downloaded from Sigma-Aldrich on Nov. 3, 2020. (Year: 2020).*
Arik Dahan et a , Title: The twofold advantage of the amorphous form as an oral drug delivery practice for lipophilic compounds: increased apparent solubility and drug flux through the intestinal membrane; AAPS J. Apr. 2013; vol. 5(2); pp. 347-353; published Epub Dec. 15, 2012) (Year: 2012).*
Alvir, et al., "Clozapine-Induced Agranulocytosis," *The New England Journal of Medicine*, vol. 329, No. 3, pp. 162-167, (1993).
Avendano, et al., "The problem of the existence of C(Ar)—H . . . N Intramolecular Hydrogen Bonds in a Family of 9-Azaphenyl-9H-carbazoles," *J. Chem. Soc. Perkin Trans.*, vol. 2, pp. 1547-1555, (1993).
Baille, T.A., "The Use of Stable Isotopes in Pharmacological Research," *Pharmacol. Reviews*, vol. 33, No. 2, pp. 81-132, (1981).
Balbach, et al., "Pharmaceutical evaluation of early development candidates 'the 100 mg-approach'", *International Journal of Pharmaceutics*, vol. 275, pp. 1-12, (2004).
Bastin, et al.,"Salt Selection and Optimisation Procedures for Pharmaceutical New Chemical Entities", *Organic Process and Research Development*, vol. 4, No. 5, pp. 427-435 (2000).
Beletskaya, et al., "Pd- and Cu-catalyzed selective arylation of benzotriazole," *Tetrahedron Letters*, vol. 39, pp. 5617-5620, (1998).
Bennett, et al., "Cecil Textbook of Medicine," 20th Edition, vol. 1, pp. 1004-1010, (1996).
Berger, et al., "Synthesis of some conformationally restricted analogs of fentanyl." *Journal of Medicinal Chemistry*, vol. 20, No. 4, pp. 600-602, (1977).
Boger, et al., "Inverse Electron Demand Diels-Alder Reactions of Heterocyclic Aza Dienes. Studies on the Total Synthesis of Lavendamycin: Investigative Studies on the Preparation of the CDE β-Carboline Ring System and AB Quinoline-5,8-quinone Ring System" *J. Org. Chem.*, vol. 50, pp. 5782-5789, (1985).
Bowman, et al., "Intramolecular Aromatic Substitution (SRN1) Reactions—Use of Entrainment for the Preparation of Benzothiazoles," *Tetrahedron Letters*, vol. 23, pp. 5093-5096, (1982).
Bowman, et al., "Copper (1) Catalysed Aromatic Nucleophilic Substitution: A Mechanistic and Synthetic Comparison with the $S_{RN}$1 Reaction", *Tetrahedron Letters*, vol. 25, No. 50, pp. 5821-5824, (1984).
Bowman, et al.,"Synthesis of 1H-quinazoline-4-ones Using Intramolecular Aromatic Nucelophilic Substitution," *ARKIVOC*, vol. x, pp. 434-442 (2003).
Bremner, et al., "Neuroimaging of Posttraumatic Stress Disorder", *Psychiatric Annals Journal*, vol. 28, No. 8, p. 445-450, (1998).
Browne, T.R., "Stable Isotope Techniques in Early Drug Development: An Economic Evaluation," *J. Clin. Pharmacol.*, vol. 38, pp. 213-220, (1998).
Bryan-Lluka, et al., "Potencies of Haloperidol Metabolites as Inhibitors of the Human Noradrenaline, Dopamine and Serotonin Transporters in Transfected COS-7 Cells", *Naunyn-Shemiedeberg's Arch Pharmacol*, vol. 360, pp. 109-115, (1999).
Byrn, et al., "Pharmaceutical Solids: A Strategic Approach to Regulatory Considerations," *Pharmaceutical Research*, vol. 12, No. 7, pp. 945-954, (1995).
Caira, M.R., "Crystalline Polymorphism of Organic Compounds," *Topics in Current Chemistry*, vol. 198, p. 163-203, (1998).
Crawford, et al., "Copper-Catalyzed Amidations of Bromo Substituted Furans and Thiophenes," *Tetrahedron Letters*, vol. 43, pp. 7365-7368, (2002).
Darmani, et al., "Do Functional Relationships Exist Between 5-HT$_{1A}$ and 5-HT$_2$ Receptors?" *Pharmacology and Biochemistry & Behavior*, vol. 36, pp. 901-906, (1990).
Davis, et al., "ITI-007 in the Treatment of Schizophrenia: From Novel Pharmacology to Clinical Outcomes," *Expert Review of Neurotherapeutics*, vol. 16, No. 6, pp. 601-614, (2016).
Evindar, et al., "Copper- and Palladium-Catalyzed Intramolecular Aryl Guanidinylation: An Efficient Method for the Synthesis of 2-Aminobenzimidazoles", *Organic Letters*, vol. 5, No. 2, pp. 133-136, (2003).
Ezquerra, et al., "Efficient Reagents for the Synthesis of 5-, 7-, and 5, 7-Substitued Indoles Starting from Aromatic Amines: Scope and Limitations", *J. Org. Chem.*, vol. 61, pp. 5804-5812, (1996).
Fawcett, J., "Posttraumatic Stress Disorder, Stress, and Happiness", *Psychiatric Annals Journal*, vol. 28, No. 8, pp. 427-428, (1998).
Fee, et al., "Copper (II)-Promoted Solvolyses of Nickel (II) Complexes III. Tetradentate Schiff Base Ligands Containing Various Diamine Segments," *Aust. J. Chem.*, vol. 26, pp. 1475-1485, (1973).
Ferreira, et al., "Novel Synthetic Routes to Thienocarbazoles via Palladium or Copper Catalyzed Amination or Amidation of Arylhalides and Intramolecular Cyclization", *Tetrahedron*, vol. 58, pp. 7943-7949, (2002).
Finet, et al., "Recent Advances in Ullmann Reaction: Copper (II) Diacetate Catalysed N-, )- and S-arylation Involving Polycoordinate Heteroatomic Derivatives," *Current Organic Chemistry*, vol. 6, pp. 597-626, (2002).
Foster, et al., "Acetylcholinesterase inhibitors reduce spreading activation in dementia," *Neuropsychologia*, vol. 50, pp. 2093-2099, (2012).
Friedman, M.J.., "Current and Future Drug Treatment for Posttraumatic Stress Disorder Patients", *Psychiatric Annals Journal*, vol. 28, No. 8, pp. 464-468, (1998).
Goodbrand, et al., "Ligand-Accelerated Catalysis of the Ullmann Condensation: Application to Hole Conducting Triarylamines," *J. Org. Chem.*, vol. 64, pp. 670-674, (1999).
Grant, D., "Theory and Origin and Polymorphism", *Polymorphism in Pharmaceutical Solids*, Chapter 1, pp. 1-10, (1999).
Guillory, J.K., "Generation of Polymorphs, Hydrates, Solvates, and Amorphous Solids", *Polymorphism in Pharmaceutical Solids*, Chapter 5, pp. 183-226, (1999).
Hackam, et al., "Translation of Research Evidence from Animals to Humans," *JAMA*, vol. 296, No. 14, pp. 1731-1732, (2006).

(56) References Cited

OTHER PUBLICATIONS

Hamann, et al., "Systematic Variation of Bidentate Ligands Used in Aryl Halide Amination. Unexpected Effects of Steric, Electronic, and Geometric Perturbations", *J. Am. Chem. Soc.*, vol. 120, pp. 3694-3703, (1998).
Harbert, et al., "Neuroleptic Activity in 5-Aryltetrahydro-y-carbolines", *J. Med. Chem.*, vol. 23, pp. 635-643, (1980).
Hartwig, J., "Palladium-Catalyzed Amination of Aryl Halides: Mechanism and Rational Catalyst Design," *Synlett*, pp. 329-340, (1996).
Harvey, et al., "Serotonin and Stress: Protective or Malevolent Actions in the Biobehavioral Response to Repeated Trauma?," *Annals of the New York Academy of Sciences*, vol. 1032, pp. 267-272, (2004); DOI: 10.1196/annals.1314.035.
Hassan, et al., "Aryl-aryl Bond Formation One Century After the Discovery of the Ullmann Reaction," *Chem. Rev.*, vol. 102, pp. 1359-1469, (2002).
Haynes, et al., "Occurrence of Pharmaceutically Acceptable Anions and Cations in the Cambridge Structural Database", *Journal of Pharmaceutical Sciences*, vol. 94, No. 10, pp. 2111-2120, (2005).
Howland, R.H., "Deuterated Drugs," Journal of Psychosocial Nursing and Mental Health Services, 53(9): 13-16 (2015).
International Preliminary Report on Patentability for International Application No. PCT/US2013/036514 dated Oct. 14, 2014.
International Search Report issued in International Application No. PCT/US2008/003340, dated Aug. 8, 2008, 3 pages.
International Search Report issued in International Application No. PCT/US2009/001608, dated Apr. 27, 2009, 3 pages.
International Search Report issued in International Application No. PCT/US2009/003261, dated Jul. 16, 2009.
International Search Report issued in International Application No. PCT/US2011/00719, dated Jul. 5, 2011, 3 pages.
International Search Report issued in International Application No. PCT/US2013/036515, dated Aug. 13, 2013, 3 pages.
International Search Report issued in International Application No. PCT/US2013/036514, dated Aug. 16, 2013, 3 pages.
International Search Report issued in International Application No. PCT/US2013/036512, dated Aug. 19, 2013, 4 pages.
International Search Report issued in International Application No. PCT/US2017/054962, dated Nov. 27, 2017, 3 pages.
Ito, et al., "Studies of Organic Catalytic Reactions. VI. The Function of Pyridine and Copper in the Rosenmund-von Braun Reaction," *Bulletin of the Chemical Society of Japan*, vol. 41, pp. 419-423, (1968).
Izrayelit, L., "Schizoaffective Disorder and PTSD Successfully Treated With Olanzapine and Supportive Psychotherapy", *Psychiatric Annals Journal*, vol. 28, No. 8, pp. 424-426, (1998).
Jain et al., "Polymorphism in Pharmacy", *Indian Drugs*, vol. 23, No. 6, pp. 315-316, (1986).
Ji, et al., "Selective Amination of Polyhalopyridines Catalyzed by a Palladium-xantphos Complex," *Organic Letters*, vol. 5, No. 24, pp. 4611-4614, (2003).
Jordan, V.C., "Tamoxifen: A Most Unlikely Pioneering Medicine," *Nature Reviews: Drug Discovery*, vol. 2, pp. 205-213, (2003).
Kahn, et al., "Residual Symptoms of Schiziphrenia. What are Realistic Treatment Goals? Lingering Symptoms Require you to Evaluate Pharmacotherapy and Offer Psychosocial Interventions," *Current Psychiatry*, vol. 16, No. 3, pp. 35-40, (2017).
Kametani, et al., "A Novel Synthesis of Indole Derivatives," *Heterocycles*, vol. 14 No. 3, pp. 277-280, (1980).
Kang, et al., "Copper-catalyzed N-arylation of Aryl Iodides with Benzamides or Nitrogen Heterocycles in the Presence of Ethylendiamine," *Synlett*, No. 3, pp. 427-430, (2002).
Kay, et al., "The Positive and Negative Syndrome Scale (PANSS) for Schizophrenia," *Schizophrenia Bulletin*, vol. 13, No. 2, pp. 261-276, (1987).
Kessler, et al., "Lifetime Prevalence and Age-of-Onset Distributions of DSM-IV Disorders in the National Comorbidity Survey Replication," *Arch Gen Psychiatry*, vol. 62, pp. 593-602, (2005).

Khorana, et al., "Gamma-Carbolines: Binding at 5-HT5A Serotonin Receptors," *Bioorganic & Medicinal Chemistry*, vol. 11, pp. 717-722, p. 718 Table 1, (2003).
Kiyomori, et al., "An Efficient Copper-catalyzed Coupling of Aryl Halides with Imidazoles," *Tetrahedron Letters*, vol. 40, pp. 2657-2660, (1999).
Klapars, et al., "A General and Efficient Copper Catalyst for the Amidation of Aryl Halides and the N-arylation of Nitrogen Heterocycles," *J. Am. Chem. Soc.*, vol. 123, pp. 7727-7729, (2001).
Klapars, et al., "A General and Efficient Copper Catalyst for the Amidation of Aryl Halides," *J. Am. Chem. Soc.*, vol. 124, pp. 7421-7428, (2002).
Kondratov, et al., "Nucelophilic Substitution in the Aromatic Series. Lv. Reaction of o-nitrochlorobenzene with Ammonia in the Presence of Copper Compounds," *Zhurnal Organidreskoi Khimii*, vol. 51, No. 11, pp. 2387-2390, (1979).
Koppel, et al., "Optimal Treatment of Alzheimer's Disease Psychosis: Challenges and Solutions," *Neuropsychiatric Disease and Treatment*, vol. 10, pp. 2253-2262, (2014).
Kwong, et al., "Mild and Efficient Copper-catalyzed Amination of Aryl Bromides with Primary Alkylamines," *Organic Letters*, vol. 5, No. 6, pp. 793-796, (2003).
Lebert, et al., "Trazodone in Fronto-Temporal Dementia," *Research and Practice in Alzheimer's Disease*, vol. 11, pp. 356-360, (2006).
Lee, et al. "Novel, Highly Potent, Selective $5-HT_{2A}/D_2$ Receptor Antagonists as Potential Atypical Antipsychotics," *Bioorg. Med. Chem. Lett.*, vol. 13, pp. 767-770, (2003).
Li, et al., "Discovery of a Tetracyclic Quinoxaline Derivative as a Potent and Orally Active Multifunctional Drug Candidate for the Treatment of Neuropsychiatric and Neurological Disorders," *Journal of Medicinal Chemistry*, vol. 57, pp. 2670-2682, (2014).
Lieberman, et al., "ITI-007 for the Treatment of Schizophrenia: A 4-Week Randomized, Double-Blind, Controlled Trial," *Biol. Psychiatry*, vol. 79, No. 12, pp. 952-961, (2015).
Lin, et al., "Dosage and Duration of Antipsychotic Treatment in Demented Outpatients with Agitation or Psychosis," *Journal of the Formosan Medical Association*, vol. 114, pp. 147-153, (2015).
Lipschitz, et al., "Childhood Posttraumatic Stress Disorder: A Review of Neurobiologic Sequelae," *Psychiatric Annals Journal*, vol. 28, No. 8, pp. 452-457, (1998).
Lopez, et al., "Psychiatric Symptoms Vary with the Severity of Dementia in Probably Alzheimer's Disease," *J. Neuropsychiatry Clin. Neurosc.*, vol. 15, No. 3, pp. 346-353, (2003).
Louie, et al., "Palladium-Catalyzed Synthesis of Arylamines from Aryl Halides, Mechanistic Studies lead to Coupling in the Absence of Tin Reagents", *Tetrahedron Letters*, vol. 36, No. 21, pp. 3609-3612, (1995).
Lounkine, et al., "Formal Concept Analysis for the Identification of Molecular Fragment Combinations Specific for Active and Highly Potent Compounds," *J. Med. Chem.*, vol. 51, No. 17, pp. 5342-5348, (2008).
Madhusoodanan, S., et al., "Pharmacological Management of Behavioral Symptoms Associated with Dementia," *World J. Psychiatr.*, vol. 4, No. 4, pp. 72-79, (2014).
March, et al., *Advanced Organic Chemistry; Reactions, Mechanisms and Structures*, Fourth Edition, pp. 910-911, (1992).
Marcoux, et al., "A General Copper-catalyzed Synthesis of Diaryl Ethers," *J. Am. Chem. Soc.*, vol. 119, pp. 10539-10540, (1997).
Mohamed, et al., "Pharmacotherapy of PTSD in the U.S. Department of Veterans Affairs: Diagnostic- and Symptom-guided Drug Selection," *J. Clin. Psychiatry*, vol. 69, pp. 959-965, (2008).
Morgan, et al., "Acoustic Startle in Individuals With Posttraumatic Stress Disorder," *Psychiatric Annals Journal*, vol. 28, Issue 8, pp. 430-434, (1998).
Mulrooney, et al., "Recent Developments in Copper-catalyzed N-arylation with Aryl Halides," *Essay—University of Pennsylvania*, (2004).
Murakami, et al., "Fischer Indolization of Ethyl Pyruvate 2-[2-(Trifluoromethyl) phenyl]-phenylhydrazone and New Insight into the Mechanism of the Goldberg Reaction," *Chem. Pharm. Bull*, vol. 43, No. 8, pp. 1281-1286, (1995).

(56) References Cited

OTHER PUBLICATIONS

Nagai, et al., "Synthesis of 2,3,4,4a,5,9b-hexahydro-1H-pyrido[4,3-b] indole Derivatives and Their Central Nervous System Activities," *Journal of Medicinal Chemistry*, vol. 22, No. 6, pp. 677-683, (1979).
Newman, et al., "Solid-state Analysis of the Active Pharmaceutical Ingredient in Drug Products," *Drug Discovery Today*, vol. 8, No. 9, pp. 898-903, (2003).
Noble, et al., "The Opiod Receptors as Targets for Drug Abuse Medication," *British Journal of Pharmacology*, vol. 172, pp. 3964-3979, (2015); DOI: 10.1111/bph.13190.
Palanisamy, M. et al., "Cellulose-Based Matrix Microspheres of Prednisolone Inclusion Complex; Preparation and Characterization." American Association of Pharmaceutical Scientists PharmSciTech, vol. 12, No. 1, pp. 388-400, (2011).
Pieniaszek, et al., "Moricizine Bioavailability via Simultaneous Dual, Stable Isotope Administration: Bioequivalence Implications," *J. Clin. Pharmacol.*, vol. 39, pp. 817-825, (1999).
Pine, et al., "Dopamine, Time, and Impulsivity in Humans," *The Journal of Neuroscience*, vol. 30, No. 26, pp. 8888-8896.
Pond, et al., "Stereospecific Reduction of Haloperidol in Human Tissues," *Biochemical Pharmacology*, vol. 44, No. 5, pp. 867-871, (1992).
"Protection for the Amino Group," *Protective Groups in Organic Synthesis*, Third Edition, John Wiley & Sons, Inc., pp. 494-505, (1999).
Rackova, et al., "Free Radical Scavenging and Antioxidant Activities of Substituted Hexahydropyridoindoles. Quantitative Structure-Activity Relationships." *Journal of Medicinal Chemistry*, vol. 49, No. 8, pp. 2543-2548, (2006).
Rainer, M.K., "Risperidone Long-acting Injection: A Review of its Long Term Safety and Efficacy," *Neuropsychiatric Disease and Treatment*, vol. 4, No. 5, pp. 919-927, (2008).
RYE (Sleep Disorders and Parkinson's Disease, 2000, accessed online http://www.waparkinsons.org/edu_research/articles/Sleep_Disorders.html), 2 pages.
Sadighi, et al., "A Highly Active Palladium Catalyst System for the Arylation of Anilines," *Tetrahedron Letters*, vol. 39, pp. 5327-5330, (1998).
Savjani, et al., "Drug Solubility: Importance and Enhancement Techniques," *International Scholarly Research Network Pharmaceutics*, vol. 2012, pp. 1-10, (2012).
Schennach, et al., "What Are Residual Symptoms in Schizophrenia Spectrum Disorder? Clinical Description and 1-year Persistence Within a Naturalistic Trial," *Eur. Arch. Psychiatry Clin. Neurosci.*, vol. 265, pp. 107-116, (2015); DOI: 10.1007/s00406-014-0528-2.
"Securities," Bennett v. Alkermes, Inc., at http://securities.stanford.edu/filings-documents/1029/ALKS03-01/20031029_r01c_0312091.pdf (retrieved from the internet on Jun. 13, 2017), (2003).
Seishinkei Shi, vol. 110, No. 7, pp. 557-584, (2008) in Japanese and with a partial English translation.
Sigel, et al., "Tenary Complexes in Solution," *Inorganic Chemistry*, vol. 13, No. 2, pp. 462-465, (1974).
Singhal, et al., "Drug Polymorphism and Dosage Form Design: A Practical Perspective," *Advanced Drug Delivery Reviews*, vol. 56, pp. 335-347, (2004).
Skoog, et al., *Principles of Instrumental Analysis*, Fourth Edition, pp. 577, (1992).
Smith, et al., "Oxford Dictionary of Biochemistry and Molecular Biology", *Oxford University Press*, pp. 145, (1997).
Snyder, et al., "Functional Profile of a Novel Modulator of Serotonin, Dopamine, and Glutamate Neurotransmission," *Psychopharmacology*, vol. 232, pp. 605-621, (2015); Published online Aug. 2014, DOI 10.1007/s00213-014-3704-1.
Southwick, et al., "Neuroendocrine Alterations in Posttraumatic Stress Disorder," *Psychiatric Annals Journal*, vol. 28, No. 8, pp. 436-442, (1998).
Sugahara, et al., "A Facile Copper-Catalyzed Ullman Condensation: N-Arylation of Heterocyclic Compounds Containing an—NHCO-Moiety," *Chem. Pharm. Bull.*, vol. 45, No. 4, pp. 719-721, (1997).

Suzuki, H. et al., "Comparison of Nicotinamide, Ethyluirea and Polyethylene Glycol as Carriers for Nifedipine Solid Dirperssion Systems." *Chemical and Pharmaceutical Bulletin*, vol. 45, No. 10, pp. 1688-1693, (1997).
Taragano, et al., "A Double-Blind, Randomized, Fixed-Dose Trial of Fluoxetine vs. Amitriptyline in the Treatment of Major Depression Complicating Alzheimer's Disease," *Psychosomatics*, vol. 38, No. 3, pp. 246-252, (1997).
Tariot, et al., "Memantine Treatment in Patients with Moderate to Severe Alzheimer Disease Already Receiving Donepezil: A Randomized Controlled Trail," *JAMA*, vol. 291, No. 3, pp. 317-324, (2004).
Timmins, G.S., "Deuterated drugs: where are we now?" *Expert Opinion on Therapeutic Patents*, 1-9 (2014).
Wagaw, et al., "A Palladium-catalyzed Method for the Preparation of Indoles via the Fischer Indole Synthesis," *Journal of the American Chemical Society*, vol. 121, No. 44, pp. 10251-10263, (1999).
Weschules, et al., "Acetylcholinesterase Inhibitor and N-Methyl-D-Aspartic Acid Receptor Antagonist Use among Hospice Enrollees with a Primary Diagnosis of Dementia," *Journal of Palliative Medicine*, vol. 11, No. 5, pp. 738-745, (2008).
Wiese, M., "DSC Detection of Polymorphism in Pharmaceutical Anhdrous Dexamethasone Acetate," *TA Instruments*, TA302, pp. 1-4, (2002).
Wolfe, et al., "An Improved Catalyst System for Aromatic Carbon-nitrogen Bond Formation: The Possible Involvement of bis(phosphine) Palladium Complexes as Key Intermediates," *JACS*, vol. 118, pp. 7215-7216, (1996).
Wolfe, et al., "Intramolecular Palladium-catalyzed Aryl Amination and Aryl Amidation," *Tetrahedron*, vol. 52, No. 21, pp. 7525-7546, (1996).
Wolter, et al., "Synthesis of N-aryl Hydrazines by Copper-catalyzed Coupling of Hydrazides with Aryl Iodides," *Organic Letters*, vol. 3, No. 23, pp. 3803-3805, (2001).
Written Opinion of the International Searching Authority for International Application No. PCT/US2013/036514 dated Aug. 16, 2013, 4 pages.
Written Opinion of the International Searching Authority for International Application No. PCT/US2017/054962 dated Nov. 27, 2017, 8 pages.
Yamada, et al., "A Mild Copper-mediated Intramolecular Amination of Aryl Halides," *Synlett*, No. 2, pp. 231-234, (2002).
Yang, B.H., "The Development of Efficient Protocols for the Palladium-catalyzed Cyclization Reactions of Secondary Amides and Carbamates," *Organic Letters*, vol. 1, No. 1, pp. 35-37, (1999).
Yudofsky, et al., "Propranolol in the Treatment of Rage and Violent Behavior in Patients with Chronic Brain Syndromes," *Am. J. Psychiatry*, vol. 138, pp. 218-220, (1981).
Zhang, et al., "Highly Efficient Copper-catalyzed N-arylation of Alkylamines with Aryl Iodides Using Phosphoramidite as Ligand," *Catalysis Communications*, vol. 6, pp. 784-787, (2005).
Zhang, et al., "The Role of Serotonin 5-HT2A Receptors in Memory and Cognition," *Front. Pharmacol.*, vol. 6, No. 225, pp. 1-17, (2015); DOI: 10.3389/fphar.2015.00225.
Press Release, "Intra-Cellular Therapies Announces Additional Results from Phase I/II Clinical Trial for ITI-007 in Healthy Geriatric Subjects and Patients With Dementia," Intra-Cellular Therapies, Press Release Date: Nov. 21, 2014, (http://ir.intracellulartherapies.com/releasedetail.cfm?ReleaseID=884325), accessed on May 31, 2016.
Aiken, C., "An Overview of Atypical Antipsychotics for Bipolar Depression," published on Jan. 3, 2020 at https://www.psychiatrictimes.com/view/overview-atypical-antipsychotics-bipolar-depression, 11 pages.
Angst et al. "Prevalence and Characteristics of Undiagnosed Bipolar Disorders in Patients With a Major Depressive Episode", Arch Gen Psychiatry, vol. 68(8), p. 701-709, (2011).
Bechtold, D.A., et al., "Circadian Dysfunction in Disease," Trends in Pharmacological Sciences, vol. 31, No. 5, pp. 191-198, (2010); DOI: 10.1016/j.tips.2010.01.002. Abstract only.
Cole, P., "ITI-007. 5-HT2A receptor antagonist, dopamine D2 receptor modulator, treatment of schizophrenia, treatment of insom-

(56) References Cited

OTHER PUBLICATIONS nia," Drugs of the Future, vol. 40, No. 10, pp. 643-650, (2015); DOI: 10.1358/dof.2015.040.10.2387229.

Davis et al., "ITI-007: A Novel Treatment for Behavioral Disturbances Associated with Dementia and Related Disorders," Clinical Trials in Alzheimer's Disease (CTAD) Congress 2014 (2014) (poster presentation).

Davis et al., "Rationale for the Development of Low Doses of ITI-007 for the Treatment of Behavioral Disturbances Associated with Dementia," The Journal of Prevention of Alzheimer's Disease, 2(4):302 (2015) (Clinical Trials in Alzheimer's Disease (CTAD) Congress, Symposium Summary OC51).

Davis, et al., "ITI-007 demonstrates brain occupancy at serotonin 5-HT2A and dopamine D2 receptors and serotonin transporters using positron emission tomography in healthy volunteers," Psychopharmacology, vol. 232, pp. 2863-2872, (2015); DOI: 10.1007/s00213-015-3922-1.

Davis, et al., "Lumateperone (ITI-007), A Novel Drug in Development for the Treatment of Agitation in Patients with Dementia, including Alzheimer's Disease: Rationale and Clinical Design," The Journal of Prevention of Alzheimer's Disease, 4(4):372 (2017) (Clinical Trials in Alzheimer's Disease (CTAD) Congress, Symposium Summary P93.

Dhawan et al., "Sleep-related Problems of Parkinson's Disease," Age and Ageing, vol. 35, pp. 220-228, (2006); DOI: 10.1093/ageing/afj087.

Ellenbroek et al., "Animal Models for the Negative Symptoms of Schizophrenia," Behavioural Pharmacology, vol. 11, pp. 223-233, (2000).

Fletcher, P., et al., "Perceiving is Believing: A Bayesian Approach to Explaining the Positive Symptoms of Schizophrenia," Nature Reviews/Neuroscience, vol. 10, pp. 48-58, (2009).

Gramigna, J, "Lumateperone Safe, Effective for Depressive Symptoms Among Patients with Bipolar Disorders," American Society of Clinical Psychopharmacology Annual Meeting, Jun. 2, 2020, 3 pages.

Harbert, C.A. et al., "Neuroleptic Activity in 5-Aryltetrahydro-y-carbolines", J. Med. Chem., vol. 23, pp. 635-643 (1980).

Hlavinka, E., "Schizophrenia Tx Eases Depression in Bipolar Disorder: Lumateperone Offers Greater Rate of Response, Remission versus Placebo," Medpage Today, 7 pages, (2020); https://www.medpagetoday.com/meetingcoverage/psychcongress/88584.

Krystal, J.H., et al., "Adjunctive Risperidone Treatment for Antidepressant-Resistant Symptoms of Chronic Military Service-Related PTSD: A Randomized Trial," JAMA, vol. 306, No. 5, pp. 493-502, (2011).

Lammers, et al., "Risperidone Long-acting Injection in Schizophrenia Spectrum Illnesses Compared to First Generation Depot Antipsychotics in an Outpatient Setting in Canada," BMC Psychiatry, vol. 13, No. 155, 9 pages, (2013); http://www.biomedcentral.com/1471-244X/13/155.

Laughren, et al., "Food and Drug Administration Commentary on Methodological Issues in Negative Symptom Trials," Schizophrenia Bulletin, vol. 37, No. 2, pp. 255-256, (2011), doi: 10.1093/schbul/sbq162.

Makadia et al., "Poly Lactic-co-Glycolic Acid (PLGA) as Biodegradable Controlled Drug Delivery Carrier," Polymers (Basel), vol. 3, No. 3, pp. 1377-1397, (2011).

Marek et al. Synergistic Action of 5-HT2A Antagonists and Selective Serotonin Reuptake Inhibitors in Neuropsychiatric Disorders. Neuropsychopharmacology, 2003. vol. 28, pp. 402-412, (Year: 2003).

Medisorb Fact Sheet in Medisorb Microspheres Technology (Jan. 2009) at https://static.secure.website/wscfus/6472891/uploads/Medisorb.pdf (retrieved from the internet May 18, 2020) (Year: 2009).

Mueller, et al., "Detection of Depression in Acute Schizophrenia: Sensitivity and Specificity of 2 Standard Observer Rating Scales," Can J Psychiatry, vol. 51, No. 6, pp. 387-392, (2006).

Mulrooney, C., et al., "Recent developments in copper-catalyzed n-arylation with aryl halides," Essay—University of Pennsylvania (2004).

O'Gorman, et al., "Lumateperone (ITI-007): A Novel Investigational Agent with Broad Therapeutic Potential Across Multiple Neuropsychiatric Disorders," Poster P.l.g.038, European College of Neuropsychopharmacology (ECNP) Congress (2017).

Perlis et al., "Clinical Features of Bipolar Depression Versus Major Depressive Disorder in Large Multicenter Trials", Am J Psychiatry, vol. 163, p. 225-231, (2006).

Pubchem, OPEN Chemistry Database, PubChem SID 103920954, PubChem CID 90655118, (2011), 6 pages.

Reynolds, C.A., et al., "Longitudinal Change in Memory Performance Associated with HTR2A Polymorphism," Neurobiology of Aging, vol. 27, pp. 150-154, (2006).

Satlin, et al., "ITI-007 (Lumateperone) for the Treatment of Agitation in Patients with Dementia, including Alzheimer's Disease," Alzheimer's & Dementia 14(7) (Suppl.): P678-79 (2018) (Alzheimer's Assoc. International Conference 2018, summary of Poster P2-032).

Satlin, et al., "ITI-007 (Lumateperone) for the Treatment of Agitation in Patients with Dementia, including Alzheimer's Disease," Poster P2-032, Alzheimer's Assoc. International Conference 2018 (2018).

"Study of a Novel Antipsychotic ITI-007 in Schizophrenia," Clinical Trials.gov, 6 pages, Dec. 26, 2011.

Tohen, M., et al., "Efficacy of Olanzapine and Olanzapine-Fluoxetine Combination in the Treatment of Bipolar I Depression," Arch Gen Psychiatry, vol. 60, pp. 1079-1088, (2003).

Vanover, et al., "A Novel Approach to Address an Unmet Need in the Treatment of Schizophrenia and Depression: Lumateperone, an Innovative Modulator of Dopamine, Serotonin, and Glutamate," Abstract presented at the American Society of Clinical Psychopharmacology (ASCP) Annual Meeting; May 29-Jun. 1, 2018; Miami, FL.

Vanover, et al., "Dopamine D2 receptor occupancy of lumateperone (ITI-007): a Positron Emission Tomography Study in patients with schizophrenia," Neuropsychopharmacology 44:598-605, (2019).

Vanover, K., et al., "ITI-007: A Novel Therapy for the Treatment of Schizophrenia and Related Psychoses," International Clinical Psychopharamcology, vol. 26, e56, 1 page, (2011).

Vloeberghs, E., et al., "Altered Circadian Locomotor Activity in APP23 Mice: A Model for BPSD Disturbances," European Journal of Neuroscience, vol. 20, pp. 2757-2766, (2004); DOI: 10.1111/j.1460-9568.2004.03755.x.

Vyas, P., et al., "An Evaluation of Lumateperone Tosylate for the Treatment of Schizophrenia," Expert Opinion on Pharmacotherapy, vol. 21, No. 2, pp. 139-145, (2020); https://doi.org/10.1080/14656566.2019.1695778.

Warner-Schmidt, et al., "Antidepressant Effects of Selective Serotonin Reuptake Inhibitors (SSRIs) are Attenuated by Antiinflammatory Drugs in Mice and Humans," PNAS, vol. 108, No. 22, pp. 9262-9267, (2011).

Wennogle, et al., "Activation of NMDA and AMPA Receptors by Lumateperone (ITI-007): Implications for Antidepressant Activity," Abstract presented at the 2017 Collegium Internationale Neuro-Psychopharmacologicum (CINP) Thematic Meeting: Treatment Resistant Depression; Jul. 20-22, 2017; Prague.

* cited by examiner

AMORPHOUS SOLID DISPERSIONS

CROSS REFERENCE TO RELATED APPLICATIONS

This application is a United States application under 35 U.S.C. § 371 claiming priority to and the benefit of International Application No. PCT/US2017/054962, filed on Oct. 3, 2017, which claims priority to and the benefit of U.S. Provisional Application Ser. No. 62/407,285, filed on Oct. 12, 2016, the contents of each of which are hereby incorporated by reference in their entireties.

FIELD

This disclosure relates to certain novel amorphous solid dispersion formulations of a substituted heterocycle fused gamma-carboline, the manufacture of such dispersions, pharmaceutical compositions comprising such dispersions, and uses thereof, e.g., in the treatment of diseases or abnormal conditions involving or mediated by the 5-HT$_{2A}$ receptor, serotonin transporter (SERT), and/or dopamine D$_1$/D$_2$ receptor signaling pathways.

BACKGROUND 1-(4-fluoro-phenyl)-4-((6bR,10aS)-3-methyl-2,3,6b,9,10, 10a-hexahydro-1H,7H-pyrido[3',4':4,5]pyrrolo[1,2,3-de] quinoxalin-8-yl)-butan-1-one (sometimes referred to as 4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone, or Lumateperone or as ITI-007), has the following structure:

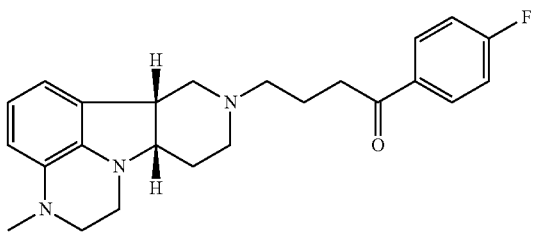 [SMILES: CN1CCN2c3c(cccc31)[C@@H]1CN(CCCC(=O)c3ccc(F)cc3)CC[C@@H]12]

ITI-007 is a potent 5-HT$_{2A}$ receptor ligand (Ki=0.5 nM) with strong affinity for dopamine (DA) D2 receptors (K$_i$=32 nM) and the serotonin transporter (SERT) (K$_i$=62 nM), but negligible binding to receptors associated with cognitive and metabolic side effects of antipsychotic drugs (e.g., H1 histaminergic, 5-HT$_{2C}$, and muscarinic receptors). ITI-007 is currently in clinical trials, i.e., for the treatment of schizophrenia. While ITI-007 is a promising drug, its production and formulation present distinct challenges. In free base form, ITI-007 is an oily, sticky solid, with poor solubility in water. Making salts of the compound has proven to be unusually difficult. A hydrochloride salt form of ITI-007 was disclosed in U.S. Pat. No. 7,183,282, but this salt was hygroscopic and shows poor stability. A toluenesulfonic acid addition salt (tosylate) of ITI-007 was finally identified and described in WO 2009/114181. Both of these publications are incorporated by reference in their entirety.

Nevertheless, there remains a need for alternative stable, pharmaceutically acceptable solid forms of ITI-007 which can be readily incorporated into galenic formulations.

It has been disclosed that for a number of drugs, amorphous forms exhibits different dissolution characteristics, and in some cases different bioavailability patterns, compared to crystalline forms of the same drug. For some therapeutic indications, one bioavailability pattern may be favored over another. For example, an amorphous form of Cefuroxime axetil exhibits higher bioavailability than the crystalline form. Thus, amorphous solid dispersions are a promising alternative to traditional crystalline active pharmaceutical ingredients.

Pure amorphous drug forms tend to be unstable. As amorphous forms are thermodynamically unstable relative to the corresponding crystal forms, it is well known that amorphous forms would revert back to the stable crystalline form. This usually occurs during storage under various humidity and temperature conditions. Therefore, in order to utilize the amorphous form of a drug, it is necessary to stabilize it to inhibit crystallization of the drug active during the period of product storage.

Discovering suitable excipients that will stabilize the amorphous form of a pharmaceutical drug is a challenge, as some excipients will chemically react with the drug or promote its decomposition, while other excipients will form uniform solid dispersions that are not physically stable, not chemically stable or both.

SUMMARY

Given the difficulties involved in making salts of ITI-007, it was decided to explore whether the compound could be formulated as a physically and chemically stable amorphous solid dispersion. An extensive screen of excipients was undertaken, using various combinations of agents at different ratios and using different production methods. Dispersions were evaluated based on physical appearance and texture, X-ray powder diffraction (XRPD), modulated differential scanning calorimetry (mDSC), thermogravimetric analysis (TGA), and high-performance liquid chromatography (HPLC). Sixteen potential excipients were screened under a total of forty-four conditions, and three pharmaceutically acceptable amorphous solid dispersions were discovered.

The present disclosure provides three amorphous solid dispersions of ITI-007 free base comprising (1) ITI-007 free base at a 5:95 to 50:50 weight ratio to cellulose acetate excipient; (2) ITI-007 free base at a 25:75 to 75:25 weight ratio to cellulose acetate phthalate excipient; and (3) ITI-007 free base at a 25:75 to 75:25 weight ratio to hydroxypropylmethyl cellulose phthalate excipient.

The disclosure thus provides novel amorphous solid dispersion forms of ITI-007 free base, which dispersions are especially advantageous for use in the preparation of galenic formulations, together with methods of making and using the same.

Further areas of applicability of the present invention will become apparent from the detailed description provided hereinafter. It should be understood that the detailed description and specific examples, while indicating preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

Figure 1:
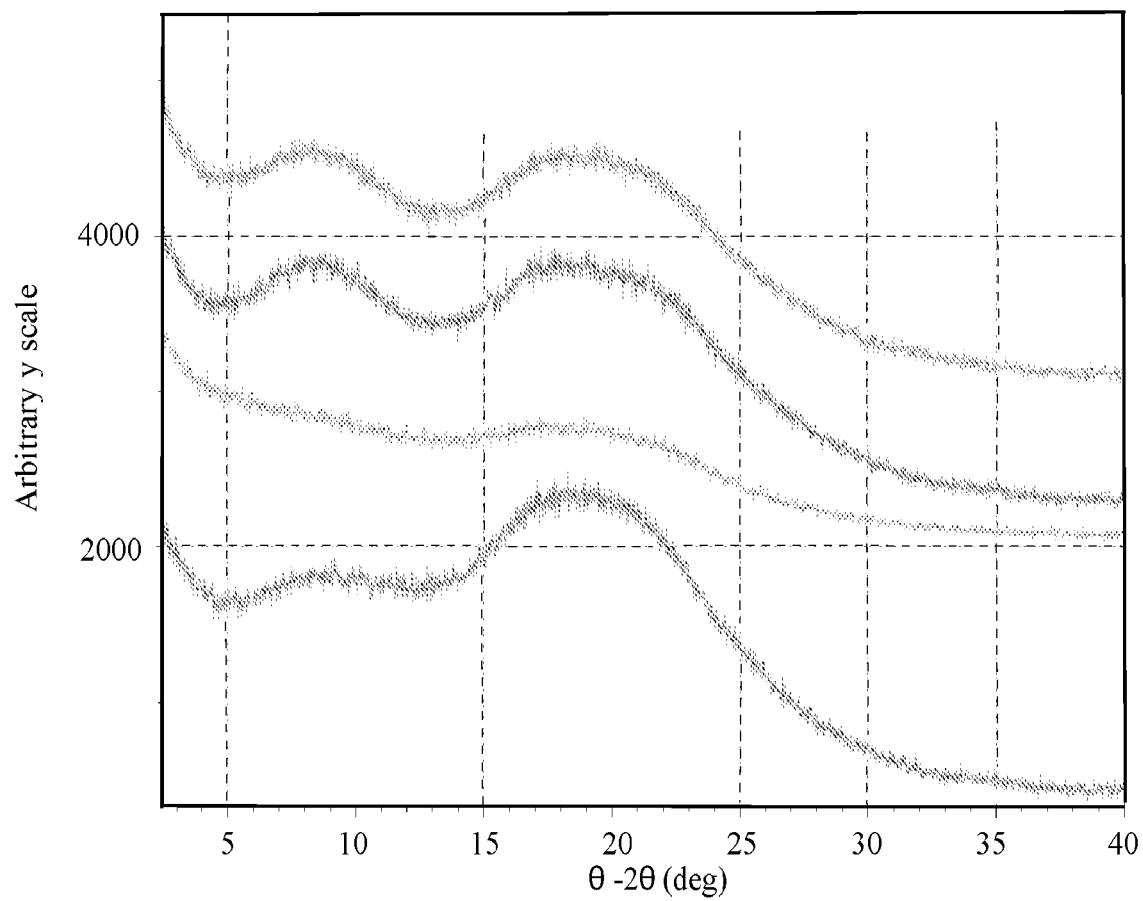
FIG. 1 depicts an overlay of X-ray powder diffraction patterns for dispersions of ITI-007 free base with cellulose acetate.
Figure 2:
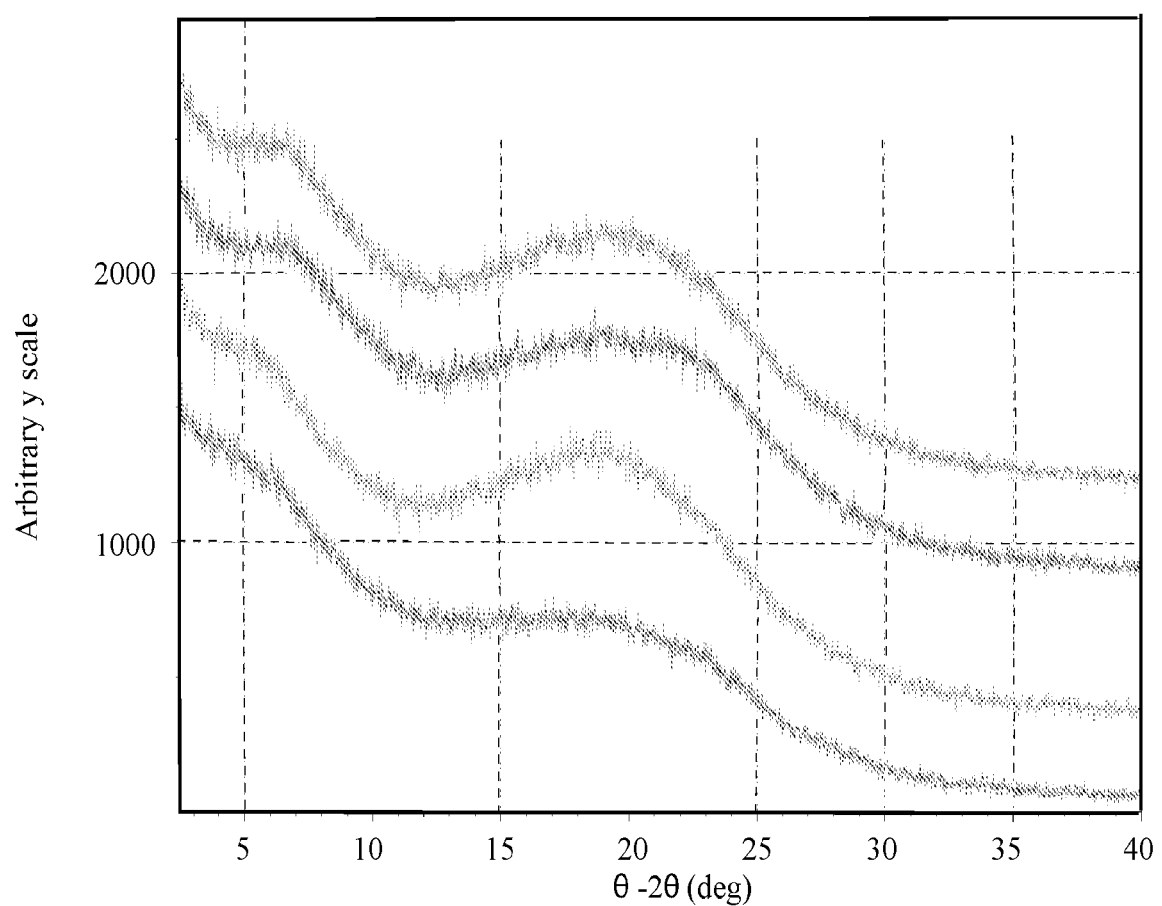
FIG. 2 depicts an overlay of X-ray powder diffraction patterns for dispersions of ITI-007 free base with cellulose acetate phthalate.
Figure 3:
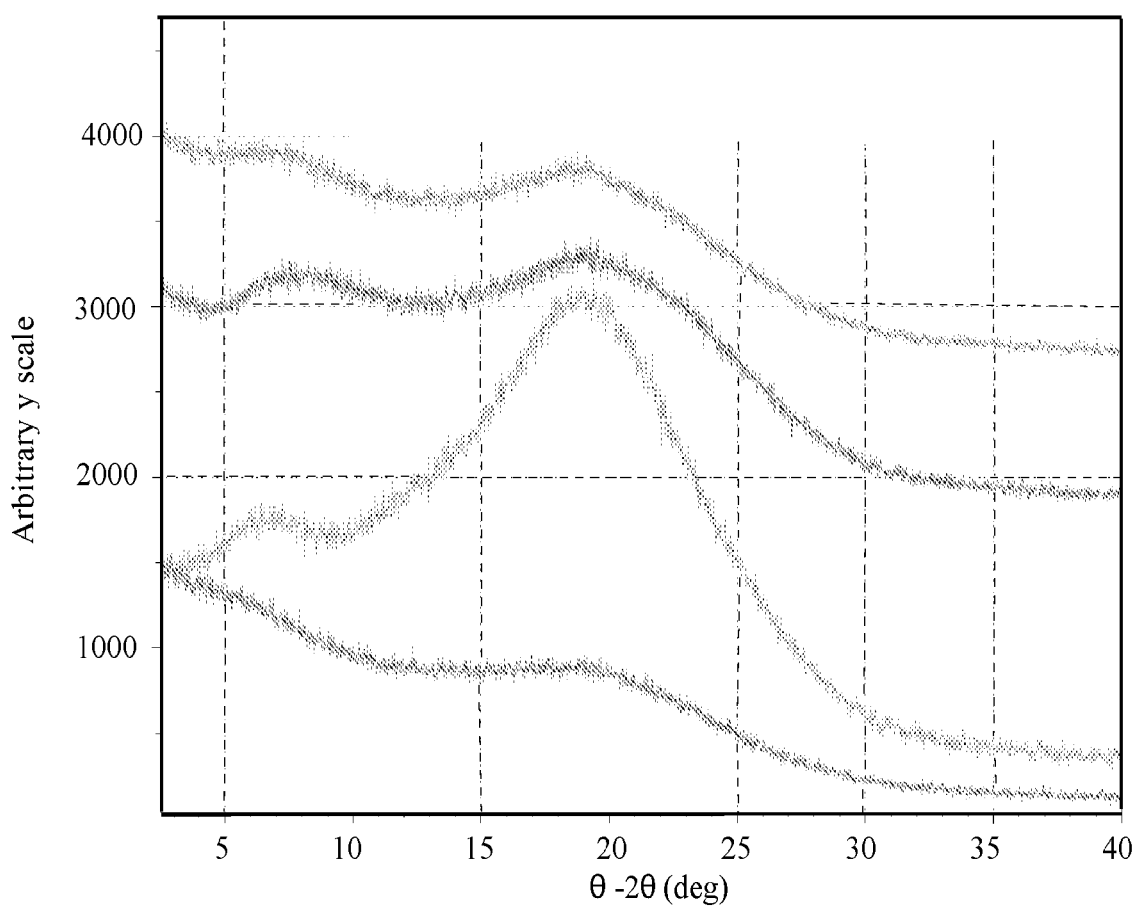
FIG. 3 depicts an overlay of X-ray powder diffraction patterns for dispersions of ITI-007 free base with hydroxypropylmethyl cellulose phthalate (grade 55) (HPMC-P).

For each of FIGS. 1, 2 and 3, the top pattern is the 25:75 ITI-007 free base/excipient dispersion as-generated; the second pattern is the 25:75 dispersion post-stress; the third pattern is the 50:50 ITI-007 free base/excipient dispersion as-generated; the bottom pattern is the 50:50 dispersion post-stress.

Figure 4:
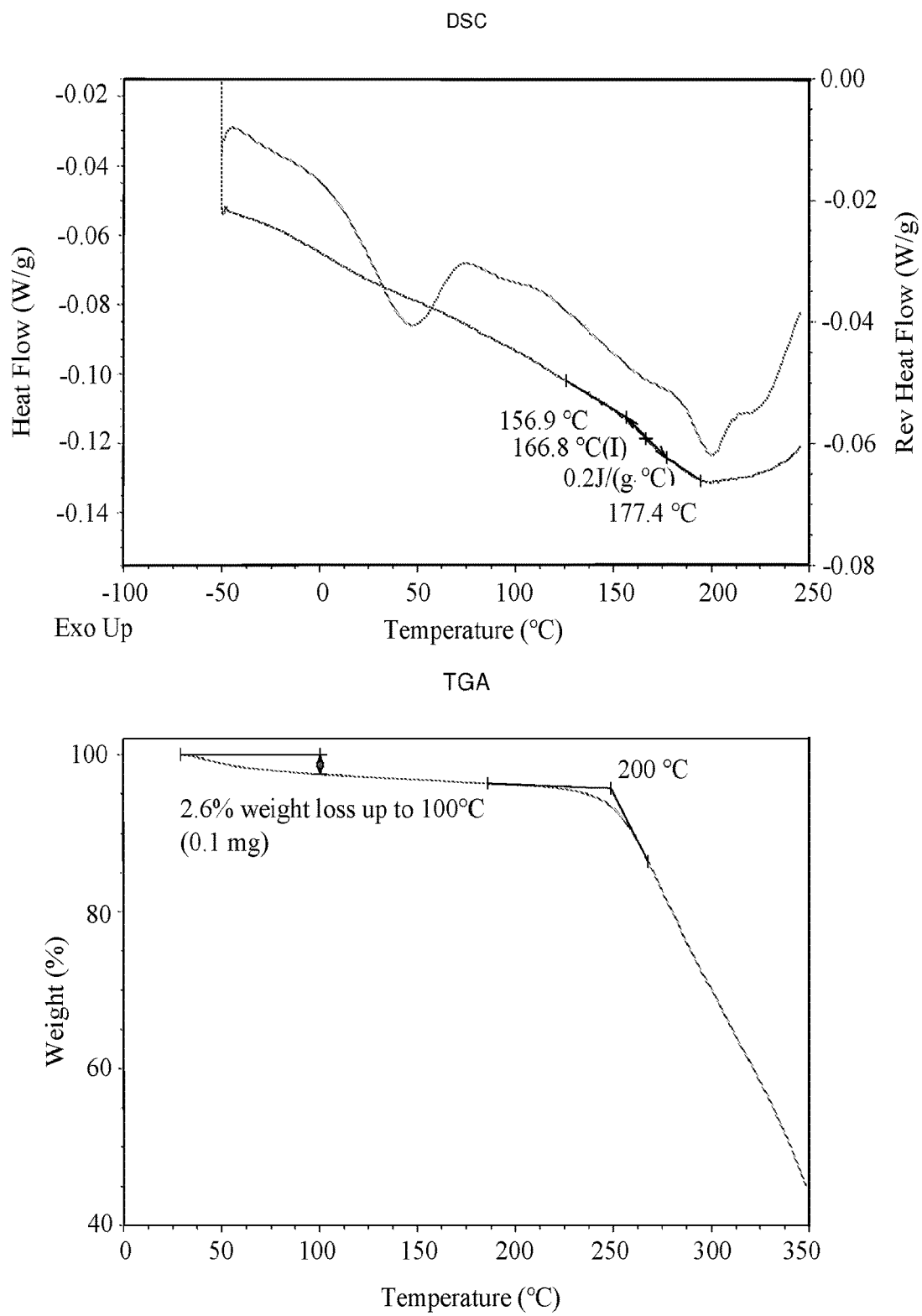

FIG. 4 depicts mDSC and TGA thermograms for a 25:75 dispersion of ITI-007 free base with cellulose acetate.

Figure 5:
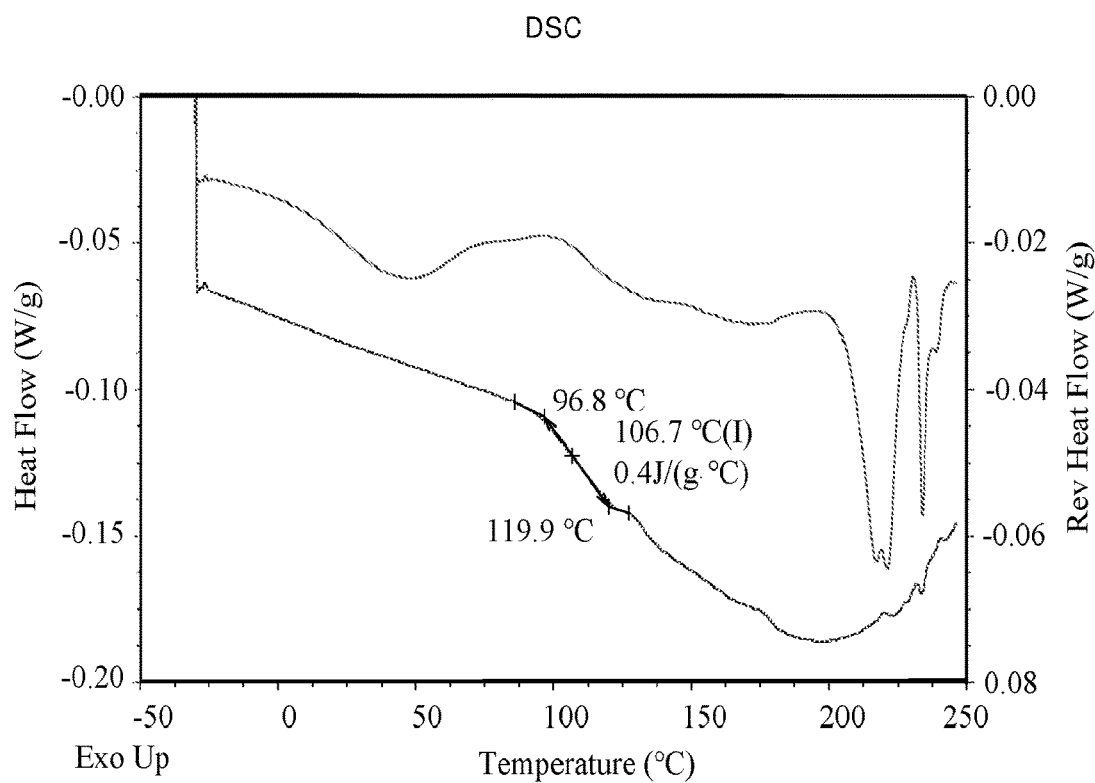
Figure 5:
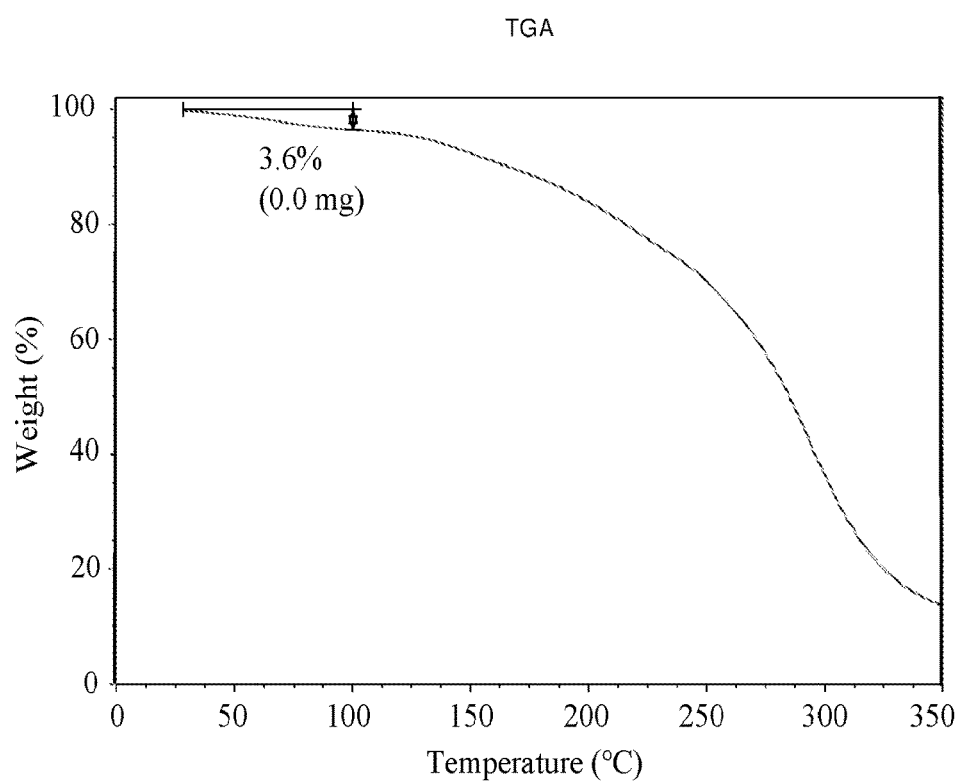

FIG. 5 depicts mDSC and TGA thermograms for a 50:50 dispersion of ITI-007 free base with cellulose acetate phthalate.

Figure 6:
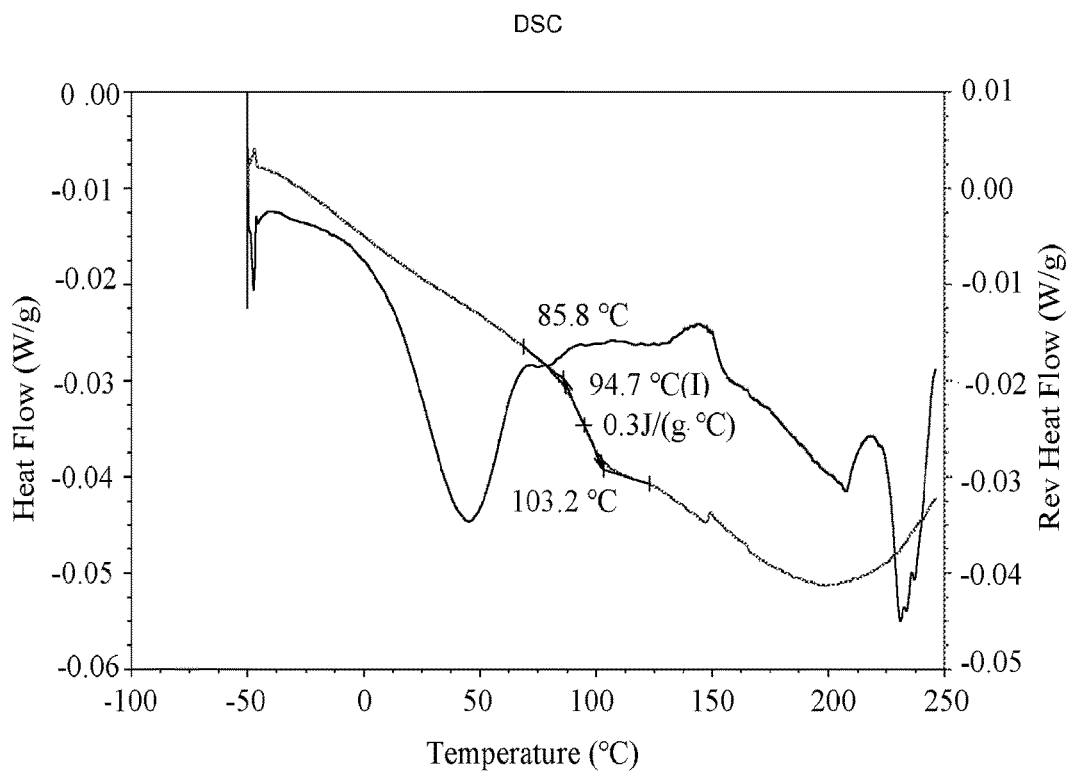
Figure 6:
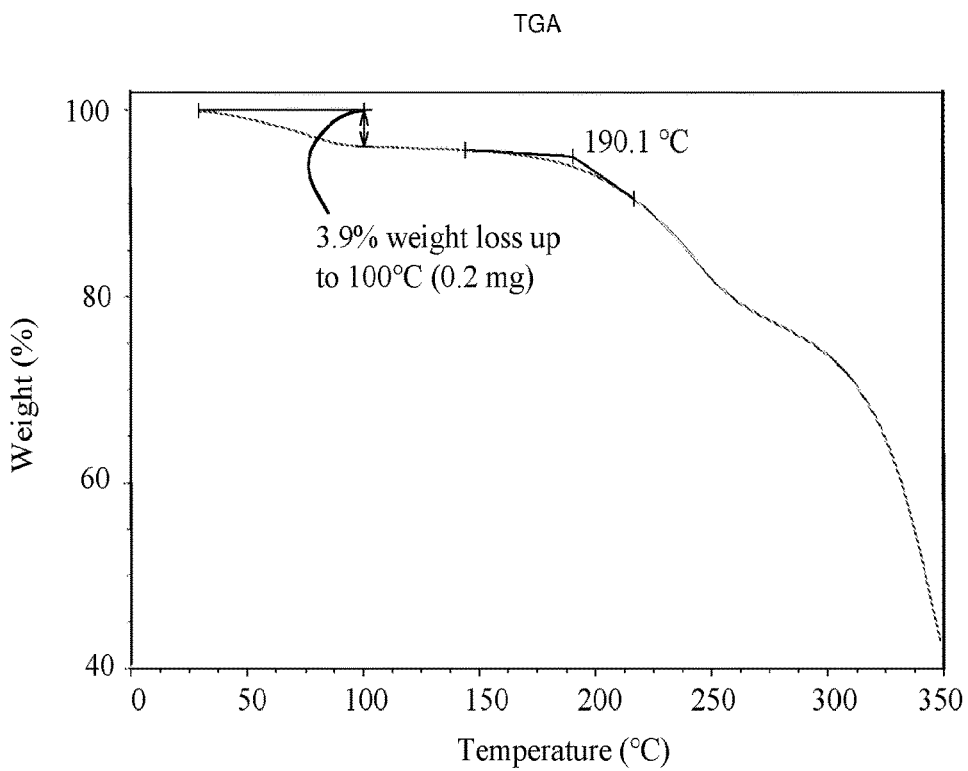

FIG. 6 depicts mDSC and TGA thermograms for a 50:50 dispersion of ITI-007 free base with HPMC-P.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

In a first embodiment, the present disclosure provides 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) free base in the form of an amorphous solid dispersion comprising cellulose acetate excipient in a ratio of 5:95 to 50:50 ITI-007 free base to cellulose acetate (Dispersion 1). The present disclosure further provides the following Compositions:

1.1. Dispersion 1, wherein the dispersion comprises ITI-007 free base and cellulose acetate in a weight ratio of 5:95 up to 50:50, but excluding the ratio 50:50.

1.2. Dispersion 1 or 1.1, wherein the dispersion comprises ITI-007 free base and cellulose acetate in a weight ratio of 5:95 to 49:51, e.g., 5:95 to 45:55, or 10:90 to 40:60, or 15:85 to 35:65, or 20:80 to 30:70, or 22:78 to 28:82, or 23:77 to 27:83, or 24:76 to 26:74, or about 25:75.

1.3. Any foregoing dispersion, wherein the dispersion is x-ray amorphous, e.g., as shown by XRPD analysis.

1.4. Any foregoing dispersion, wherein the X-ray diffraction pattern is free of peaks characteristic of the excipient.

1.5. Any foregoing dispersion, wherein the dispersion shows a single glass transition temperature ($T_g$) above 75° C., e.g., at a temperature above 100° C., or at a temperature above 150° C., e.g., as shown by mDSC analysis.

1.6. Dispersion 1.5, wherein the dispersion shows a single glass transition temperature above 160° C., or between 165° C. and 170° C., or at about 167° C.

1.7. Any foregoing dispersion, wherein the dispersion shows a change in heat capacity ($\Delta Cp$) of 0.1 to 0.5 J/g-° C., e.g., from 0.2 to 0.3 J/g-° C., or about 0.2 J/g-° C., e.g., as shown by mDSC.

1.8. Any foregoing dispersion, wherein the dispersion shows less than 10% weight loss up to a temperature of 100° C., e.g., as shown by TGA analysis.

1.9. Dispersion 1.8, wherein the dispersion shows less than 8% weight loss up to a temperature of 100° C., e.g., less than 7% weight loss, or less than 6% weight loss, or less than 5% weight loss, or less than 4% weight loss, or less than 3% weight loss, up to a temperature of 100° C.

1.10. Any foregoing dispersion, wherein the dispersion shows no changes in appearance or texture after 7 days at 75% relative humidity at 40° C.

1.11. Any foregoing dispersion, wherein the dispersion shows greater than 90% chemical stability of ITI-007 after 7 days at 75% relative humidity at 40° C., e.g., as judged by HPLC.

1.12. Dispersion 1.11, wherein the dispersion shows greater than 95%, or greater than 96%, or greater than 97% or greater than 98%, or greater than 99% chemical stability of ITI-007 after 7 days at 75% relative humidity at 40° C.

1.13. Any foregoing dispersion, wherein the dispersion is manufactured by a method comprising dissolving ITI-007 free base and the selected excipient in a suitable solvent or mixture of solvents and removing the solvent, e.g., by lyophilizing the solution, to obtain the amorphous solid dispersion.

1.14. Dispersion 1.13, wherein the solvent or mixture of solvents is selected from dioxane, methanol, ethanol, tetrahydrofuran, acetone, and mixtures thereof.

1.15. Dispersion 1.13, wherein the solvent or mixture of solvents is selected from dioxane, methanol or a dioxane/methanol mixture, e.g., a 90:10 to 98:2 ratio of dioxane to methanol, or a 92:8 to 95:5 ratio, or about a 93:7 ratio of dioxane to methanol.

1.16. Any foregoing dispersion, wherein the dispersion exhibits any combination of characteristics as described in 1.1-1.15.

In a second embodiment, the present disclosure provides ITI-007 free base in the form of an amorphous solid dispersion comprising cellulose acetate phthalate excipient in a ratio of 25:75 to 75:25 ITI-007 free base to cellulose acetate phthalate (Dispersion 2). The present disclosure further provides the following Compositions:

2.1. Dispersion 2, wherein the dispersion comprises ITI-007 free base and cellulose acetate phthalate in a weight ratio of from 25:75 up to 75:25, but excluding the ratios 25:75 and 75:25.

2.2. Dispersion 2 or 2.1, wherein the dispersion comprises ITI-007 free base and cellulose acetate phthalate in a weight ratio of 26:74 to 74:26, e.g., 30:70 to 70:30, or 35:65 to 65:35, or 40:60 to 60:40, or 42:58 to 58:42, or 44:56 to 56:44, or 45:55 to 55:45, or 47:53 to 53:47, or 48:52 to 52:48, or 49:51 to 51:49, or about 50:50.

2.3. Any foregoing dispersion, wherein the dispersion is x-ray amorphous, e.g., as shown by XRPD analysis.

2.4. Any foregoing dispersion, wherein the X-ray diffraction pattern is free of peaks characteristic of the excipient.

2.5. Any foregoing dispersion, wherein the dispersion shows a single glass transition temperature ($T_g$) above 75° C., e.g., at a temperature above 85° C., or at a temperature above 95° C., e.g., as shown by mDSC analysis.

2.6. Dispersion 2.5, wherein the dispersion shows a single glass transition temperature above 100° C., or between 105° C. and 115° C., or at about 107° C.

2.7. Any foregoing dispersion, wherein the dispersion shows a change in heat capacity (ΔCp) of 0.1 to 0.6 J/g-° C., e.g., from 0.2 to 0.5 J/g-° C., or about 0.4 J/g-° C., e.g., as shown by mDSC.

2.8. Any foregoing dispersion, wherein the dispersion shows less than 10% weight loss up to a temperature of 100° C., e.g., as shown by TGA analysis.

2.9. Dispersion 2.8, wherein the dispersion shows less than 8% weight loss up to a temperature of 100° C., e.g., less than 7% weight loss, or less than 6% weight loss, or less than 5% weight loss, or less than 4% weight loss, or less than 3% weight loss, up to a temperature of 100° C.

2.10. Any foregoing dispersion, wherein the dispersion shows no changes in appearance or texture after 7 days at 75% relative humidity at 40° C.

2.11. Any foregoing dispersion, wherein the dispersion shows greater than 90% chemical stability of ITI-007 after 7 days at 75% relative humidity at 40° C., e.g., as judged by HPLC.

2.12. Dispersion 2.11, wherein the dispersion shows greater than 95%, or greater than 96%, or greater than 97% or greater than 98%, or greater than 99% chemical stability of ITI-007 after 7 days at 75% relative humidity at 40° C.

2.13. Any foregoing dispersion, wherein the dispersion is manufactured by a method comprising dissolving ITI-007 free base and the selected excipient in a suitable solvent or mixture of solvents and removing the solvent, e.g., by lyophilizing the solution, to obtain the amorphous solid dispersion.

2.14. Dispersion 2.13, wherein the solvent or mixture of solvents is selected from dioxane, methanol, ethanol, tetrahydrofuran, acetone, and mixtures thereof.

2.15. Dispersion 2.13, wherein the solvent or mixture of solvents is selected from dioxane, methanol or a dioxane/methanol mixture, e.g., a 90:10 to 98:2 ratio of dioxane to methanol, or a 92:8 to 95:5 ratio, or about a 93:7 ratio of dioxane to methanol.

2.16. Any foregoing dispersion, wherein the dispersion exhibits any combination of characteristics as described in 2.1-2.15.

In a third embodiment, the present disclosure provides ITI-007 free base in the form of an amorphous solid dispersion comprising hydroxypropylmethyl cellulose phthalate (HPMC-P) excipient in a ratio of 25:75 to 75:25 ITI-007 free base to HPMC-P (Dispersion 3). The present disclosure further provides the following Compositions:

3.1. Dispersion 3, wherein the dispersion comprises ITI-007 free base and HPMC-P in a weight ratio of from 25:75 up to 75:25, but excluding the ratios 25:75 and 75:25.

3.2. Dispersion 3 or 3.1, wherein the dispersion comprises ITI-007 free base and HPMC-P in a weight ratio of 26:74 to 74:26, e.g., 30:70 to 70:30, or 35:65 to 65:35, or 40:60 to 60:40, or 42:58 to 58:42, or 44:56 to 56:44, or 45:55 to 55:45, or 47:53 to 53:47, or 48:52 to 52:48, or 49:51 to 51:49, or about 50:50.

3.3. Any foregoing dispersion, wherein the dispersion is x-ray amorphous, e.g., as shown by XRPD analysis.

3.4. Any foregoing dispersion, wherein the X-ray diffraction pattern is free of peaks characteristic of the excipient.

3.5. Any foregoing dispersion, wherein the dispersion shows a single glass transition temperature ($T_g$) above 75° C., e.g., at a temperature above 80° C., or at a temperature above 85° C., e.g., as shown by mDSC analysis.

3.6. Dispersion 3.5, wherein the dispersion shows a single glass transition temperature above 90° C., or between 92° C. and 98° C., or at about 95° C.

3.7. Any foregoing dispersion, wherein the dispersion shows a change in heat capacity (ΔCp) of 0.1 to 0.5 J/g-° C., e.g., from 0.2 to 0.4 J/g-° C., or about 0.3 J/g-° C., e.g., as shown by mDSC.

3.8. Any foregoing dispersion, wherein the dispersion shows less than 10% weight loss up to a temperature of 100° C., e.g., as shown by TGA analysis.

3.9. Dispersion 3.8, wherein the dispersion shows less than 8% weight loss up to a temperature of 100° C., e.g., less than 7% weight loss, or less than 6% weight loss, or less than 5% weight loss, or less than 4% weight loss, or less than 3% weight loss, up to a temperature of 100° C.

3.10. Any foregoing dispersion, wherein the dispersion shows no changes in appearance or texture after 7 days at 75% relative humidity at 40° C.

3.11. Any foregoing dispersion, wherein the dispersion shows greater than 90% chemical stability of ITI-007 after 7 days at 75% relative humidity at 40° C., e.g., as judged by HPLC.

3.12. Dispersion 3.11, wherein the dispersion shows greater than 95%, or greater than 96%, or greater than 97% or greater than 98%, or greater than 99% chemical stability of ITI-007 after 7 days at 75% relative humidity at 40° C.

3.13. Any foregoing dispersion, wherein the dispersion is manufactured by a method comprising dissolving ITI-007 free base and the selected excipient in a suitable solvent or mixture of solvents and removing the solvent, e.g., by lyophilizing the solution, to obtain the amorphous solid dispersion.

3.14. Dispersion 3.13, wherein the solvent or mixture of solvents is selected from dioxane, methanol, ethanol, tetrahydrofuran, acetone, and mixtures thereof.

3.15. Dispersion 3.13, wherein the solvent or mixture of solvents is selected from dioxane, methanol or a dioxane/methanol mixture, e.g., a 90:10 to 98:2 ratio of dioxane to methanol, or a 92:8 to 95:5 ratio, or about a 93:7 ratio of dioxane to methanol.

3.16. Any foregoing dispersion, wherein the dispersion exhibits any combination of characteristics as described in 3.1-3.15.

In a second aspect, the present disclosure provides a process (Process 1) for the production of Dispersion 1, et seq., or Dispersion 2, et seq., or Dispersion 3, et seq., comprising the steps of:

(a) combining 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) free base with the selected excipient in a suitable solvent or mixture of solvents, e.g., selected from dioxane, methanol, ethanol, tetrahydrofuran, acetone, and mixtures thereof; and (b) removing the solvent and recovering the amorphous solid dispersion thus formed, e.g., by lyophilization of the solution.

In another embodiment of the second aspect, the solvent or mixture of solvents for Process 1 is selected from dioxane, methanol or a dioxane/methanol mixture, e.g., a 90:10 to 98:2 ratio of dioxane to methanol, or a 92:8 to 95:5 ratio, or about a 93:7 ratio of dioxane to methanol, optionally wherein the solvent is removed by lyophilization.

Solid dispersion, as used herein, refers to the dispersion of an active pharmaceutical ingredient, i.e., ITI-007, in an inert excipient or matrix (carrier), where the active ingredient could exist in a finely crystalline, solubilized or amorphous state. The excipient in a solid dispersion is typically a polymer. The most important role of the polymer in a solid dispersion is to reduce the molecular mobility of the pharmaceutical active to avoid phase separation and re-crystallization of the active during storage. The amorphous form of the active is associated with a higher energy state as compared to its crystalline counterpart, and therefore, significantly less external energy is required to effect dissolution (e.g., in the gastrointestinal tract or elsewhere in the body).

In a third aspect, the present disclosure provides a pharmaceutical composition (Composition 1) comprising Dispersion 1, et seq., or Dispersion 2, et seq., or Dispersion 3, et seq., in combination or association with a pharmaceutically acceptable diluent or carrier. In some embodiments, the pharmaceutical composition is in the form of a tablet or capsule for oral administration. In some embodiments, the pharmaceutical composition is in the form of a depot formulation for use as a long-acting injectable (LAI). The pharmaceutical composition may further comprise any suitable pharmaceutically acceptable excipient, such as: diluents such as starches, pregelatinized starches, lactose, powdered celluloses, microcrystalline celluloses, dicalcium phosphate, tricalcium phosphate, mannitol, sorbitol, xylitol, sugar and the like; binders such as acacia, guar gum, tragacanth, gelatin, polyvinylpyrrolidones such as polyvinylpyrrolidones (PVP K-30,K-90), poly (vinyl pyrrolidone-co-vinyl acetate) (PVP-VA) and the like, hydroxypropyl celluloses, hydroxypropyl methylcellulose, cellulose acetate, hydroxypropyl methylcellulose acetate succinate (HPMC-AS) and the like; disintegrants such as starches, sodium starch glycolate, pregelatinized starches, crospovidones, croscarmellose sodium and the like; lubricants such as stearic acid, magnesium stearate, zinc stearate and the like; glidants such as colloidal silicon dioxide and the like; solubility or wetting enhancers such as anionic or cationic or neutral surfactants; maltodextrin, complex forming agents such as various grades of cyclodextrins and resins; release rate controlling agents such as hydroxypropyl celluloses, hydroxymethyl celluloses, hydroxypropyl methylcelluloses, ethylcelluloses, methylcelluloses, various grades of methyl methacrylates, waxes and the like; and film formers, plasticizers, colorants, flavoring agents, sweeteners, viscosity enhancers, preservatives, antioxidants, and the like.

In another embodiment of the third aspect, the composition may further comprise one or more anti-oxidants, for example, tocopherol, butylated hydroxytoluene (BHT), propyl gallate (OPG), or and ascorbic acid, or the like. The inclusion of an anti-oxidant may further improve the chemical stability of the dispersions by preventing oxidative chemical degradation of the ITI-007 active. In another embodiment, the dispersion itself is formulated to include such an anti-oxidant.

In another aspect, the present disclosure provides Dispersion 1, et seq., or Dispersion 2, et seq., or Dispersion 3, et seq., or a pharmaceutical composition comprising Dispersion 1, et seq., or Dispersion 2, et seq., or Dispersion 3, et seq., e.g., Composition 1, for use in treating a disease or abnormal condition involving or mediated by the $5\text{-HT}_{2A}$ receptor, serotonin transporter (SERT), and/or dopamine $D_1/D_2$ receptor signaling pathways, e.g., a disorder selected from obesity, anorexia, bulimia, depression, anxiety, psychosis, schizophrenia, migraine, obsessive-compulsive disorder, sexual disorders, depression, schizophrenia, migraine, attention deficit disorder, attention deficit hyperactivity disorder, obsessive-compulsive disorder, sleep disorders, conditions associated with cephalic pain, social phobias, or dementia.

In another embodiment, the invention provides a method for the prophylaxis or treatment of a human suffering from a disease or abnormal condition involving or mediated by the $5\text{-HT}_{2A}$ receptor, serotonin transporter (SERT), and/or dopamine $D_1/D_2$ receptor signaling pathways, e.g., a disorder selected from obesity, anorexia, bulimia, depression, anxiety, psychosis, schizophrenia, migraine, obsessive-compulsive disorder, sexual disorders, depression, schizophrenia, migraine, attention deficit disorder, attention deficit hyperactivity disorder, obsessive-compulsive disorder, sleep disorders, conditions associated with cephalic pain, social phobias, or dementia, comprising administering to a patient in need thereof a therapeutically effective amount of Dispersion 1, et seq., or Dispersion 2, et seq., or Dispersion 3, et seq., or a pharmaceutical composition comprising Dispersion 1, et seq., or Dispersion 2, et seq., or Dispersion 3, et seq, e.g., Composition 1.

EXAMPLES

The following equipment and methods are used to isolate and characterize the exemplified co-crystal forms:

X-ray powder diffraction (XRPD): The X-ray powder diffraction studies are performed using a PANalytical X'Pert PRO MPD diffractometer using an incident beam of Cu radiation produced using an Optix long, fine-focus source. An elliptically graded multilayer mirror is used to focus Cu Ku X-ray radiation through the specimen and onto the detector. Prior to analysis, a silicon specimen is analyzed to verify the observed position of the Si (111) peak (consistent with the NIST-certified position, NIST SM 640e). A specimen of the sample is sandwiched between 3-micron thick films and analyzed in transmission geometry. A beam-stop, short antiscatter extension, and antiscatter knife edge is used to minimize the background generated by the air. Soller slits for the incident and diffracted beams are used to minimize broadening from axial divergence. Diffraction patterns are collected using a scanning position-sensitive detector (X'Celerator) located 240 mm from the specimen. Data Collector software v. 2.2b is used for analysis.

Thermogravimetry (TGA) analysis: TGA is performed using a TA Instruments Q5000 or Discovery thermogravimetric analyzer. The sample is placed in an aluminum sample pan and is inserted into the TG furnace. Samples are heated from ambient temperature to 250° C. at a rate of 10° C./minute. Nickel and Alumel are used as the calibration standards.

Modulated Differential Scanning Calorimetry (mDSC): mDSC data is obtained on a TA Instruments Q2000 or 2920 differential scanning calorimeter equipped with a refrigerated cooling system. Temperature calibration is performed using NIST traceable indium metal. The sample is placed into an aluminum T-zero DSC pan, covered with a lid, and the weight is accurately recorded. A weighed aluminum pan configured as the sample pan is placed on the reference side of the cell. Typically, the start temperature is −50° C. and the end temperature is 250° C., with a modulation amplitude of ±1° C. and a 50 second period with an underlying heating rate of 2° C. per minute.

High performance liquid chromatography (HPLC): The high-performance liquid chromatography analyses are performed using an Agilent 1100 series liquid chromatograph equipped with a diode array detector, degasser, quaternary pump, and an auto sampler. The column is a 4.6×100 mm CSH C18 column with 2.5-micron packing (XSelect) running with a 0.1% TFA in water mobile phase A and a 0.1% TFA in acetonitrile mobile phase B, at a flow rate of 0.500 mL/minute. The gradient runs from 95% A to 73% over the first 22 minutes, followed by 6 minutes at 73% A, and followed by 73% A to 30% A over the next 22 minutes. The column temperature is set to 15.0° C., and the detector wavelength is 254 nm with a bandwidth of 100 nm and a reference wavelength of 360 nm. The injection volume is 2.0 microliters.

Example 1: Preparation of Dispersions

Solubility of ITI-007 free base and various excipients is first evaluated in various solvents. It is found that ITI-007 free base shows good solubility (>50 mg/mL) in acetone, ethanol, methanol, dioxane, and 2,2,2-trifluoroethanol (TFE), but relatively poor solubility (5-50 mg/mL) in tert-butanol/water mixtures. However, it is found that solutions of ITI-007 free base in TFE rapidly discolor due to decomposition of the active.

The excipients evaluated are Eudragit L100, polyvinyl acetate, polyvinylpyrrolidone-vinyl acetate copolymer, polyvinylpyrrolidone K-90, polyvinylpyrrolidone S-630, cellulose acetate, cellulose acetate phthalate, Gelucire 50/13, glyceryl monostearate, hydroxypropyl cellulose, hydroxypropyl methyl cellulose phthalate (HPMC-P), hydroxypropyl methyl acetate succinate (HPMC-AS), polyethylene glycol (PEG), PEG-100 succinate, Pluronic F-127, and Soluplus. Excipients were evaluated at one or more of the ratios 25:75, 50:50 and 75:25 ITI-007 free base to excipient.

Based on the solubility analyses, solutions of various excipients with ITI-007 free base are prepared in 3:1 acetone-ethanol. Rotary evaporation is attempted to remove the solvent, but this results in oily materials, instead of solids, in all cases.

Solid dispersions are successfully prepared by lyophilization from solutions of ITI-007 free base and excipient in either dioxane or dioxane-methanol (90:10, 91:9, 92:8, 93:7 or 94:6). Solutions are initially frozen in a dry ice/acetone bath, and then placed in a freeze dryer with the shelf pre-cooled to −75° C. Samples are dried overnight at −50° C., followed by −20° C., then 0° C. over a period of two days. Samples are then secondary dried at 20° C. for four hours, purged with nitrogen then stored in a freezer over desiccant until testing.

Example 2: Preliminary Screen

Solid dispersions obtained from Example 1 are first evaluated by XRPD to determine if they are amorphous. All lyophilization samples using amorphous excipients are found to be x-ray amorphous by XRPD. Lyophilization samples using crystalline excipients (Gelucire 50/13, PEG, PEG-1000 succinate, Pluronic F-127) are found to be disordered with peaks present corresponding only to the excipient. Further observations of the appearance of the solids are shown in Table 1 below. The 50:50 ITI-007/PEG-1000 succinate dispersion is found to be very sticky and is not further evaluated.

Example 3: Stability Evaluation

Solid dispersions from Example 1 are placed into uncapped clear glass vials and the vials are placed into a container maintained for seven days at 75% relative humidity and a temperature of 40° C. As a control, a sample of ITI-007 free base is analyzed in parallel. Samples were observed visually as well as by polarized light microscopy (0.8-10× magnification with crossed polarizers and a first order red compensator). Observations are shown in Table 1. The majority of samples display changes in appearance or texture, indicating the formation of physically unstable amorphous dispersions. For example, some show visible crystallization while others become sticky solids or oils.

Dispersions which are physically stable free-flowing solids are further analyzed by XRPD to confirm that they remain x-ray amorphous or disordered with excipient peaks only. The XRPD results confirm that the visually stable samples remain X-ray amorphous dispersions.

mDSC and TGA analysis is conducted on the physically stable free-flowing samples. A single glass transition temperature in mDSC supports the conclusion that the solid is a non-crystalline miscible dispersion. The two PEG dispersions show an unacceptable low-temperature glass transition at 9 or 10° C., while the glyceryl monostearate dispersion shows no glass transition. The 50:50 cellulose acetate dispersion shows two glass transition temperatures, which suggests a phase-separated material, which is unacceptable. Only the 25:75 cellulose acetate, 25:75 cellulose acetate phthalate, 50:50 cellulose acetate phthalate, 25:75 HPMC-AS, 50:50 HPMC-AS, 25:75 HPMC-P and 50:50 HPMC-P dispersions show acceptable single glass transition temperatures above 75° C.

All samples submitted to mDSC and TGA are then submitted to HPLC analysis to determine the chemical stability of the ITI-007 active agent during the seven-day study. As a control, the ITI-007 free base sample is also analyzed by HPLC. All results are normalized to the ITI-007 content shown by HPLC prior to the seven-day study. A loss of less than 5% ITI-007 by HPLC is considered satisfactory.

Both HPMC-AS dispersions, as well as the 25:75 HPMC-P dispersion show very high material losses by HPLC. The 25:75 cellulose acetate phthalate dispersion shows a low but unacceptable loss of material. Only seven dispersions produce satisfactory results: 25:75 cellulose acetate, 50:50 cellulose acetate, 50:50 cellulose acetate phthalate, 50:50 HPMC-P, 25:75 PEG, 50:50 PEG and 25:75 glyceryl stearate. These dispersions are thus chemically stable.

The combined tests results are shown in Table 1 below.

| Excipient | ITI-007/ Excipient Ratio | X-ray Amorphous Solids? | Stable for 7 days at 40° C./ 75% RH | $T_g >$ 75° C. | % ITI-007 change by HPLC |
|---|---|---|---|---|---|
| Cellulose Acetate | 25:75 | Yes | Yes | Yes (167° C.) | 0% |
|  | 50:50 | Yes | Yes | No | −4.43% |
|  | 75:25 | Yes | No |  |  |
| Cellulose Acetate | 25:75 | Yes | Yes | Yes (142° C.) | −5.65% |

-continued

| Excipient | ITI-007/ Excipient Ratio | X-ray Amorphous Solids? | Stable for 7 days at 40° C./ 75% RH | $T_g >$ 75° C. | % ITI-007 change by HPLC |
|---|---|---|---|---|---|
| Phthalate | 50:50 | Yes | Yes | Yes (107° C.) | −2.42% |
| | 75:25 | Yes | No | | |
| Gelucire 50/13 | 25:75 | No | No | | |
| | 50:50 | No | No | | |
| Glyceryl Monostearate | 25:75 | No | No | No | 0% |
| | 50:50 | No | No | | |
| HPC | 25:75 | Yes | No | | |
| | 50:50 | Yes | No | | |
| HPMC-AS MG | 25:75 | Yes | | Yes (88° C.) | −55.29% |
| | 50:50 | Yes | | Yes (77° C.) | −8.76% |
| | 75:25 | Yes | No | | |
| HPMC-P | 25:75 | Yes | | Yes (123° C.) | −18.89% |
| | 50:50 | Yes | | Yes (95° C.) | −0.01% |
| | 75:25 | Yes | No | | |
| PEG | 25:75 | No | No | No | −0.30% |
| | 50:50 | No | No | No | 0% |
| | 75:25 | No | No | | |
| PEG-1000 Succinate | 25:75 | No | No | | |
| | 50:50 | No | | | |
| Pluronic F-127 | 25:75 | No | No | | |
| | 50:50 | No | No | | |
| PVAc | 25:75 | Yes | No | | |
| | 50:50 | Yes | No | | |
| PVP S-630 | 25:75 | Yes | No | | |
| | 50:50 | Yes | No | | |
| | 75:25 | Yes | No | | |
| PVP K-90 | 25:75 | Yes | No | | |
| | 50:50 | Yes | No | | |
| | 75:25 | Yes | No | | |
| PVP co-VA | 25:75 | Yes | No | | |
| | 50:50 | Yes | No | | |
| | 75:25 | Yes | No | | |
| Soluplus | 25:75 | Yes | No | | |
| | 50:50 | Yes | No | | |
| | 75:25 | Yes | No | | |
| ITI-007 only | 100:0 | No | | No | −5.97% |

Of the tested dispersions, it is found that only three are both chemically stable and physically stable: 25:75 cellulose acetate, 50:50 cellulose acetate phthalate, and 50:50 HPMC-P.

It is noted that similar experiments conducted using ITI-007 tosylate salt, instead of ITI-007 free base, result in no stable amorphous dispersions. While most of the ITI-007 tosylate dispersions pass the initial screen (X-ray amorphous or showing only X-ray peaks due to the excipient), all of the resulting initial dispersions display strong physical instability (color and appearance changes, including crystallization of the active agent out of the dispersion) or chemical instability (10-68% decomposition by HPLC). For example, the 25:75 dispersion of ITI-007 tosylate with cellulose acetate produced crystallization of ITI-007 during the aging study; the 50:50 dispersion of ITI-007 tosylate with cellulose acetate phthalate showed about a 52% decrease in ITI-007 content by HPLC; and the 50:50 dispersion of ITI-007 tosylate with HPMC-P showed about a 68% decrease in ITI-007 content by HPLC. These results are unexpected because ITI-007 tosylate is chemically more stable than ITI-007 free base. Thus, it is particularly unexpected that three specific amorphous solid dispersions of ITI-007 free base are physically and chemically stable whereas the corresponding dispersions of ITI-007 tosylate are not.

What is claimed:

1. 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) free base in the form of an amorphous solid dispersion comprising:
   (a) cellulose acetate excipient in a ratio of 5:95 to 50:50 ITI-007 free base to cellulose acetate; or
   (b) cellulose acetate phthalate excipient in a ratio of 25:75 to 75:25 ITI-007 free base to cellulose acetate phthalate; or
   (c) hydroxypropyl methyl cellulose phthalate (HPMC-P) excipient in a ratio of 25:75 to 75:25 ITI-007 free base to HPMC-P;
wherein the X-ray diffraction pattern of the amorphous solid dispersion is free of peaks characteristic of the excipient.

2. The dispersion of claim 1, wherein the dispersion comprises cellulose acetate excipient in a ratio of 5:95 to 50:50 ITI-007 free base to cellulose acetate.

3. The dispersion of claim 2, wherein the dispersion comprises ITI-007 free base and cellulose acetate in a weight ratio of 5:95 up to 50:50, but excluding the ratio 50:50.

4. The dispersion of claim 1, wherein the dispersion comprises cellulose acetate phthalate excipient in a ratio of 25:75 to 75:25 ITI-007 free base to cellulose acetate phthalate.

5. The dispersion of claim 4, wherein the dispersion comprises ITI-007 free base and cellulose acetate phthalate in a weight ratio of from 25:75 up to 75:25, but excluding the ratios 25:75 and 75:25.

6. The dispersion of claim 1, wherein the dispersion comprises HPMC-P excipient in a ratio of 25:75 to 75:25 ITI-007 free base to HPMC-P.

7. The dispersion of claim 6, wherein the dispersion comprises ITI-007 free base and HPMC-P in a weight ratio of from 25:75 up to 75:25, but excluding the ratios 25:75 and 75:25.

8. The dispersion of claim 1, wherein the dispersion is x-ray amorphous.

9. The dispersion of claim 1, wherein the dispersion shows a single glass transition temperature ($T_g$) above 75° C.

10. The dispersion of claim 1, wherein the dispersion shows less than 10% weight loss up to a temperature of 100° C.

11. The dispersion of claim 1, wherein the dispersion shows no changes in appearance or texture after 7 days at 75% relative humidity at 40° C.

12. The dispersion of claim 1, wherein the dispersion shows greater than 90% chemical stability of ITI-007 after 7 days at 75% relative humidity at 40° C.

13. The dispersion of claim 1, wherein the dispersion is manufactured by a method comprising dissolving ITI-007 free base and the selected excipient in a suitable solvent or mixture of solvents and removing the solvent to obtain the amorphous solid dispersion.

14. The dispersion of claim 13, wherein the solvent or mixture of solvents is selected from dioxane, methanol, ethanol, tetrahydrofuran, acetone, and mixtures thereof.

15. The dispersion of claim 13, wherein the solvent or mixture of solvents is selected from dioxane, methanol or a dioxane/methanol mixture.

16. The dispersion of claim 15, wherein the solvent or mixture of solvents is dioxane and methanol in a 90:10 to 98:2 ratio of dioxane to methanol, or a 92:8 to 95:5 ratio, or a 93:7 ratio of dioxane to methanol.

17. A process for the production of the dispersion of claim 1, comprising the steps of:
  (a) combining 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) free base with the selected excipient in a suitable solvent or mixture of solvents; and
  (b) removing the solvent and recovering the amorphous solid dispersion thus formed.

18. A pharmaceutical composition comprising the dispersion of claim 1, in combination or association with a pharmaceutically acceptable diluent or carrier.

19. The composition of claim 18, wherein the composition is in the form of a tablet or capsule for oral administration.

20. The composition of claim 18, wherein the composition is in the form of a depot formulation for use as a long-acting injectable (LAI).

\* \* \* \* \*

UNITED STATES PATENT AND TRADEMARK OFFICE
CERTIFICATE OF CORRECTION

PATENT NO. : 11,331,316 B2
APPLICATION NO. : 16/341806
DATED : May 17, 2022
INVENTOR(S) : Peng Li It is certified that error appears in the above-identified patent and that said Letters Patent is hereby corrected as shown below:

In the Specification

Column 8, Line 41, "Ku X-ray" should be changed to -- Kα X-ray --

Signed and Sealed this
Twenty-third Day of August, 2022

Katherine Kelly Vidal
*Director of the United States Patent and Trademark Office*